(12) United States Patent
Jungbauer et al.

(10) Patent No.: US 10,508,133 B2
(45) Date of Patent: Dec. 17, 2019

(54) PURIFICATION OF PROTEINS

(71) Applicant: NOVASEP PROCESS, Pompey (FR)

(72) Inventors: Alois Jungbauer, Vienna (AT); Ralf Sommer, Vienna (AT)

(73) Assignee: NOVASEP PROCESS, Pompey (FR)

( * ) Notice: Subject to any disclaimer, the term of this patent is extended or adjusted under 35 U.S.C. 154(b) by 4 days.

(21) Appl. No.: 15/029,682

(22) PCT Filed: Oct. 17, 2014

(86) PCT No.: PCT/IB2014/065412
§ 371 (c)(1),
(2) Date: Apr. 15, 2016

(87) PCT Pub. No.: WO2015/056237
PCT Pub. Date: Apr. 23, 2015

(65) Prior Publication Data
US 2016/0272675 A1     Sep. 22, 2016

Related U.S. Application Data

(60) Provisional application No. 61/892,975, filed on Oct. 18, 2013.

(51) Int. Cl.
*C07K 1/30* (2006.01)
*C07K 16/00* (2006.01)

(52) U.S. Cl.
CPC ............... *C07K 1/30* (2013.01); *C07K 16/00* (2013.01); *C07K 2317/10* (2013.01)

(58) Field of Classification Search
None
See application file for complete search history.

(56) References Cited

U.S. PATENT DOCUMENTS

| | | | |
|---|---|---|---|
| 3,415,804 A | 12/1968 | Polson | |
| 4,164,495 A | 8/1979 | Hansen | |
| 4,177,188 A | 12/1979 | Hansen | |
| 4,739,039 A | 4/1988 | Vasquez et al. | |
| 4,939,176 A | 7/1990 | Seng et al. | |
| 5,164,487 A | 11/1992 | Kothe et al. | |
| 5,525,519 A * | 6/1996 | Woiszwillo | C07K 1/30 436/17 |
| 5,747,031 A | 5/1998 | Ruch | |
| 2002/0177693 A1 | 11/2002 | Lebing et al. | |
| 2007/0066806 A1 | 3/2007 | Coffman et al. | |
| 2007/0244305 A1 | 10/2007 | Parkkinen | |
| 2008/0214795 A1 | 9/2008 | Ramanan et al. | |
| 2008/0249014 A1 | 10/2008 | Tauer et al. | |
| 2008/0255027 A1 | 10/2008 | Moya et al. | |
| 2010/0145022 A1 | 6/2010 | Romero et al. | |
| 2010/0150940 A1* | 6/2010 | Adam | A61K 39/3955 424/158.1 |
| 2010/0204455 A1 | 8/2010 | Gervais et al. | |
| 2012/0101262 A1 | 4/2012 | Arunakumari et al. | |
| 2014/0121357 A1 | 5/2014 | Ruiz et al. | |

FOREIGN PATENT DOCUMENTS

| | | | |
|---|---|---|---|
| EP | 14802170 | 3/2017 | |
| EP | 14802170 | 6/2017 | |
| WO | 1986005099 A1 | 9/1986 | |
| WO | WO-2005073252 A1 * | 8/2005 | ............ A61L 2/0011 |
| WO | WO-2007035283 A1 * | 3/2007 | ............... C07K 1/30 |
| WO | WO-2008127305 A2 * | 10/2008 | ............... C07K 1/34 |
| WO | WO-2009016449 A1 * | 2/2009 | ............... C07K 1/30 |
| WO | WO-2010151632 A1 * | 12/2010 | ............... C07K 1/30 |
| WO | 2015056237 A3 | 4/2015 | |
| WO | PCTIB2014065412 | 5/2015 | |
| WO | PCTIB2014065412 | 4/2016 | |

OTHER PUBLICATIONS

Liu et al. "Recovery and purification process development for monoclonal antibody production" mAbs 2:5: 480-499 (Year: 2019).*
Luviern et al. (Current Protocols in Protein Scinece, 1997, 4:5, 1-4.5.36 (Year: 1997).*
Atha, et al. Mechanism of Precipitation of Proteins by Polyethylene Glycol. J. Biol. Chem. 256(23): 12108-17 (1981).
Bergmann-Leitner, et al. Evaluation of immunoglobulin purification methods and their impact on quality and yield of antigen-specific antibodies. Malaria Journal, vol. 7, pp. 129 (2008).
Brodsky, et al. Caprylic acid precipitation method for impurity reduction: an alternative to conventional chromatography for monoclonal antibody production. Biotech. Bioeng. 109(1): 2589-2598 (2012).
Brooks et al. An improved method for the purification of IgG monoclonal antibodies from culture supernatants. J. Immunol. Meth. vol. 155, pp. 129-132 (1992).
Caprylic acid—http://en.wikipedia.org/wiki/Caprylic_acid, 3 pages (Aug. 28, 2013).
Chen, et al. The use of native cation-exchange chromatography to study aggregation and phase separation of monoclonal antibodies. Protein Science, 19(6): 1191-1204 (2010).
Dai, et al. Precipitation of Process-Derived Impurities in Non-Protein a Purification Schemes for Antibodies. Biopharm International (Oct. 2, 2009).
Edson De Souza Lucena, et al. A new methodology for polyvalent intravenous immunoglobulin solution production with a two-stage process of viral inactivation. Braz. J. Pharm. Sci. vol. 46 No. 4 São Paulo Oct./Dec. 2010.
Gibson, et al. Application of a High-Throughput Screening Procedure with PEG-Induced Precipitation to Compare Relative Protein Solubility During Formulation Development with IgG1 Monoclonal Antibodies. Journal of Pharmaceutical Sciences vol. 100 Issue: 3 pp. 1009-1021 (2011).

(Continued)

*Primary Examiner* — Daniel E Kolker
*Assistant Examiner* — James L Rogers
(74) *Attorney, Agent, or Firm* — Patrick J. Halloran

(57) ABSTRACT

This application relates to methods for purification of proteins such as antibodies using a hydrophilic polymer (e.g., PEG), a fatty acid (e.g., caprylic acid), and/or another agent (e.g., calcium chloride).

26 Claims, 20 Drawing Sheets

(56) References Cited

OTHER PUBLICATIONS

Habeeb, et al. Preparation of Human Immunoglobulin by Caprylic Acid Precipitation. Preparative Biochemistry, 14(1): 1-17 (1984).
Hammerschmidt, et al. Economics of recombinant antibody production processes at various scales: Industry-standard compared to continuous precipitation. Biotech. J. 9(6): 766-75 (2014).
Knevelman, et al. High-Throughput Screening Techniques for Rapid PEG-Based Precipitation of IgG(4) mAb from Clarified Cell Culture Supernatant. Biotechnology Progress vol. 26 Issue: 3 pp. 697-705 (2009).
Kuczewski, et al. PEG Precipitation: A Powerful Tool for Monoclonal Antibody Purification. Biopharm International Supplement: pp. 20-28, Published: Mar. 2010.
Kuczewski, et al. PEG precipitation for monoclonal antibody purification. Abstracts of Papers of the American Chemical Society vol. 241 Meeting Abstract: 103-BIOT Published: Mar. 27, 2011.
Lis, et al. Size fractionation of double-stranded DNA by precipitation with polyethylene glycol. Nuc. Acids Res. 2(3): 383-89 (1975).
Lydersen, et al. Acid Precipitation of Mammalian Cell Fermentation Broth. Annals New York Academy of Sciences 745:222-31 (1994).
Mahadaven, et al. Experimental analysis of protein precipitation by polyethylene glycol and comparison with theory Fluid Phase Equilibria, 78(C): 297-321 (1990).
McKinney, et al. A simple, non-chromatographic procedure to purify immunoglobulins from serum and ascites fuid. J Immunologic Meth. 96: 271-78 (1987).
Mohanty, et al. Purification of IgG from serum with caprylic acid and ammonium sulphate precipitation is not superior to ammonium sulphate precipitation alone, Comp. Immunol. Microbiol. Inf. Dis. 12(4): 153-60 (1989).
Morais, et al. A model mechanism for protein precipitation by caprylic acid: Application to plasma purification. Thotech. Appl. Biochem. 59(1): 50-54 (2012).
Parkkinen, et al. A modified caprylic acid method for manufacturing immunoglobulin G from human plasma with high yield and efficient virus clearance. Vox sanguinis, vol. 90, No. 2, pp. 97-104 (2006).
Perosa, et al. Purification of human immunoglobulins by sequential precipitation with caprylic acid and ammonium sulphate. J. Immunol. Meth. 128(1): 9-16 (1990).
Polson, et al. The Fractionation of Protein Mixtures by Linear Polymers of High Molecular Weight. Biochim. Biophys. Acta, 82: 463-475 (1964).
Raweerith, et al. Fractionation of equine antivenom using caprylic acid precipitation in combination with cationic ion-exchange chromatography. J. Immunol. Meth. 282(1-2): 63-72 (2003).
Rojas, et al. Caprylic acid fractionation of hyperimmune horse plasma: description of a simple procedure for antivenom production. Toxicon, 32(3): 351-363 (1994).
Russo, et al. Purification of IgG monoclonal antibody by caprylic acid precipitation. J. Immunol. Meth. 65: 269-71 (1983).
Satzer, et al. Separation of recombinant antibodies from DNA using divalent cations. Eng. In Life Sci. 14(5): 477-484 (2014).
Sim, S.L. Branched polyethylene glycol for protein precipitation (Dissertation: A Thesis Submitted for the Degree of Doctor Philosophy), pp. 1-127 (2011).
Sim et al. Protein precipitation by polyethylene glycol: A generalized model based on hydrodynamic radius. J. Biotech. 157(2): 315-19 (2012).
Sommer, et al. Continuous precipitation of therapeutic proteins, with an emphasis on monoclonal antibodies. Dissertation, Institut für angewandte Mikrobiologie (2013).
Sommer, et al. Combined polyethylene glycol and CaCl2 precipitation for the capture and purification of recombinant antibodies. Process Biochem. 49(11): 2001-9 (2014).
Steinbuch, et al. The Isolation of IgG From Mammalian Sera with the Aid of Caprylic Acid. Arch Biochem. Biophysics, 134: 279-284 (1969).
Svendsen, et al. Development and comparison of purification strategies for chicken antibodies from egg yolk. Laboratory animal science, 45(1): 89-93 (1995).
Tscheliessnig, et al. Engineering of a two-step purification strategy for a panel of monoclonal immunoglobulin M directed against undifferentiated human embryonic stem cells. J. Chromat. A. 1216(45): 7851-7864 (2009).
Vargas, et al. Purification of IgG and Albumin from Human Plasma by Aqueous Two Phase System Fractionation. Biotechnol. Prog. 28(4): 1005-1011 (2012).
Vargas, et al. Purification of IgG and albumin from human plasma by aqueous two phase system fractionation. Biotechnology progress, vol. 28, No. 4, pp. 1005-1011 (2012).
Velayudhan, et al. Continuous antibody purification using precipitation: An important step forward. Biotech. J. 9(6): 717-18 (2014).
Wang, et al. "Optimizing the primary recovery step in non-affinity purification schemes for HuMabs," BioPharm International, March supplement: 4-10 (2008).
Wang, et al. Advances in Non-Protein a Purification Processes for Human Monoclonal Antibodies. BioPharm International (Mar. 2, 2009).
Wilson, et al. Optimization of Calcium Phosphate Transfection for Bovine Chromatin Cells: Relationship to Calcium Phosphate Precipitate Formation. Anal. Biochem. 226(2): 212-220 (1995).

\* cited by examiner

FIGURE 4
A. B03
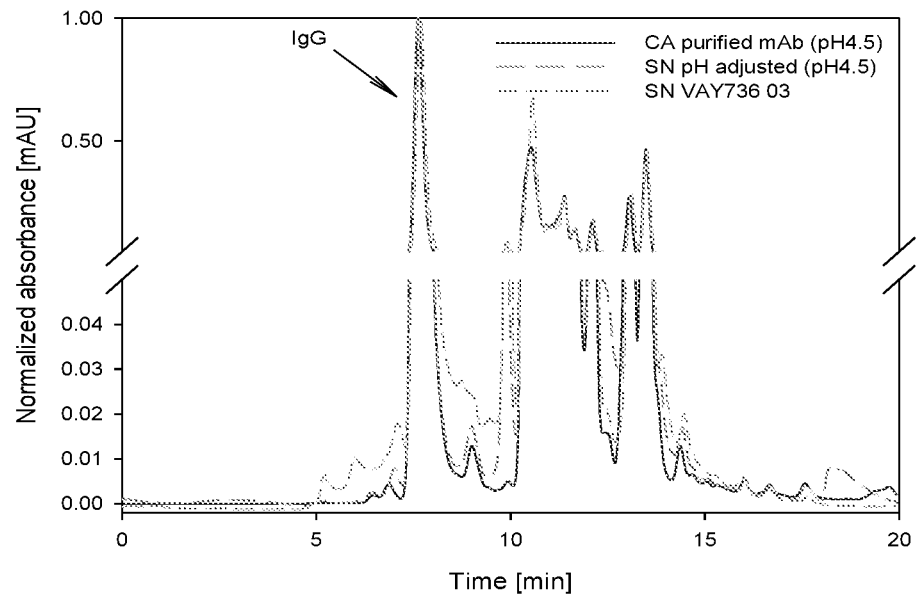
B. B07
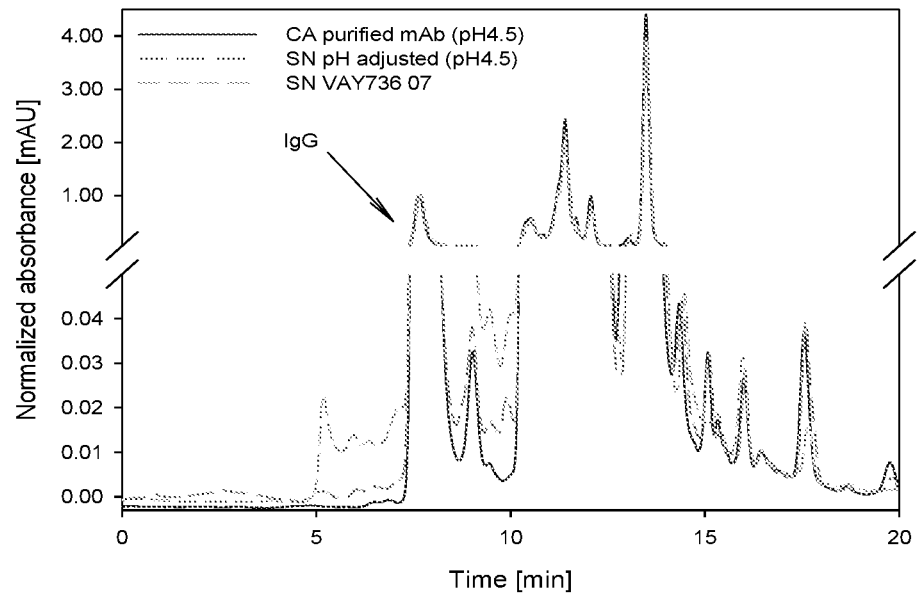

FIGURE 5
A. B03
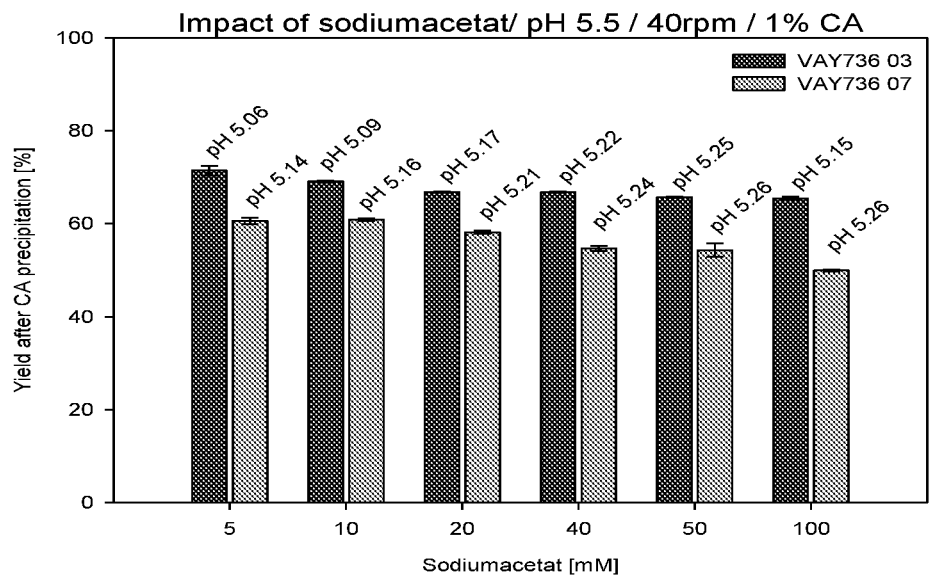
B. B07
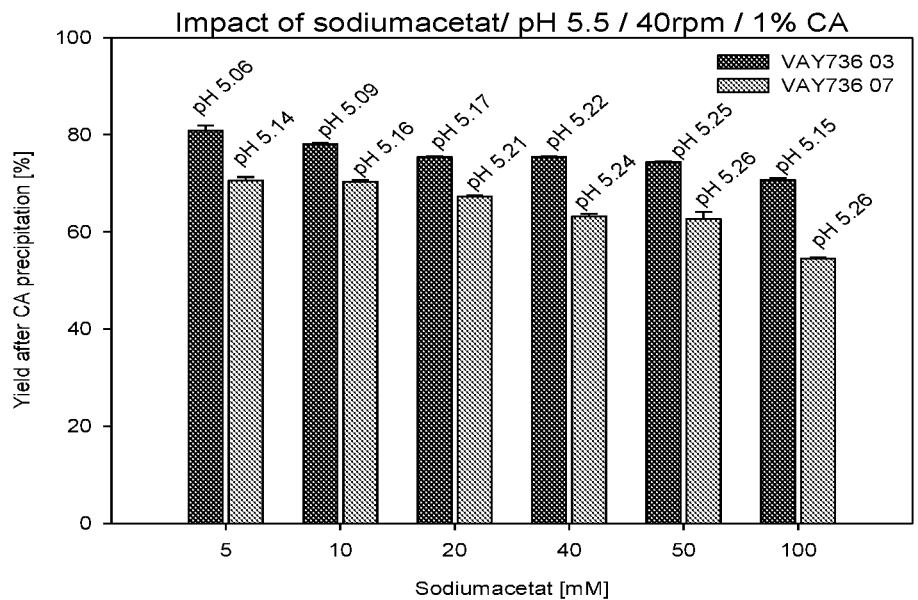

Figure 7
A. B03
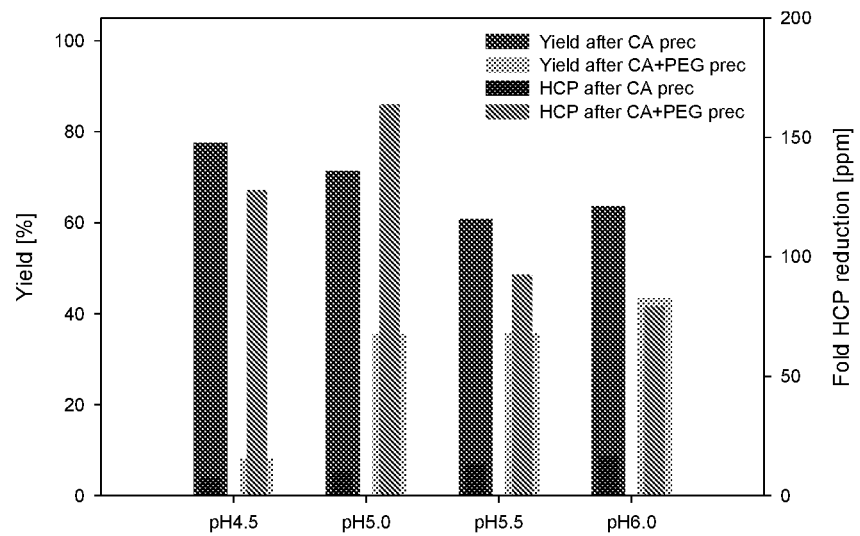
B. B07
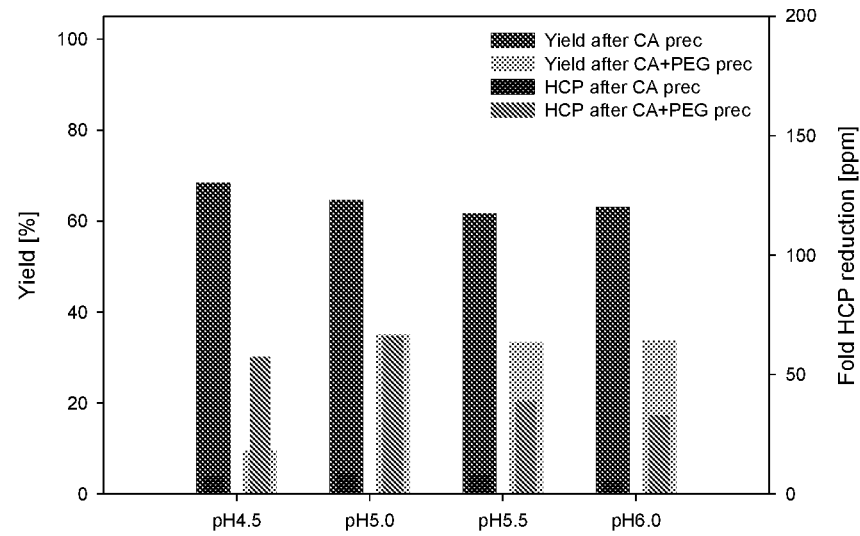

FIGURE 8
A. B03
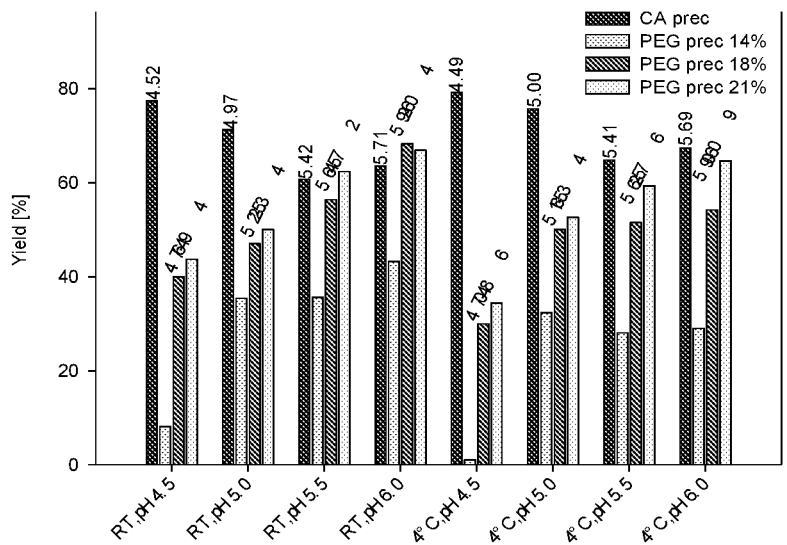
B. B07
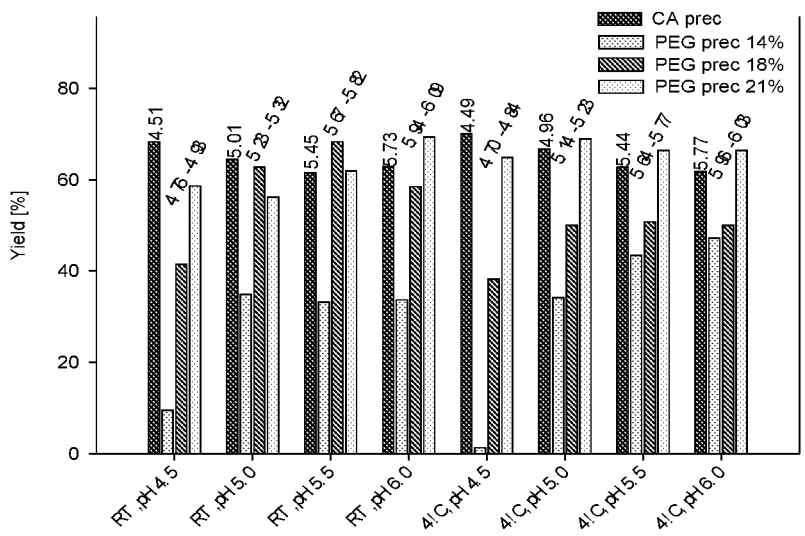

FIGURE 9
A. B03
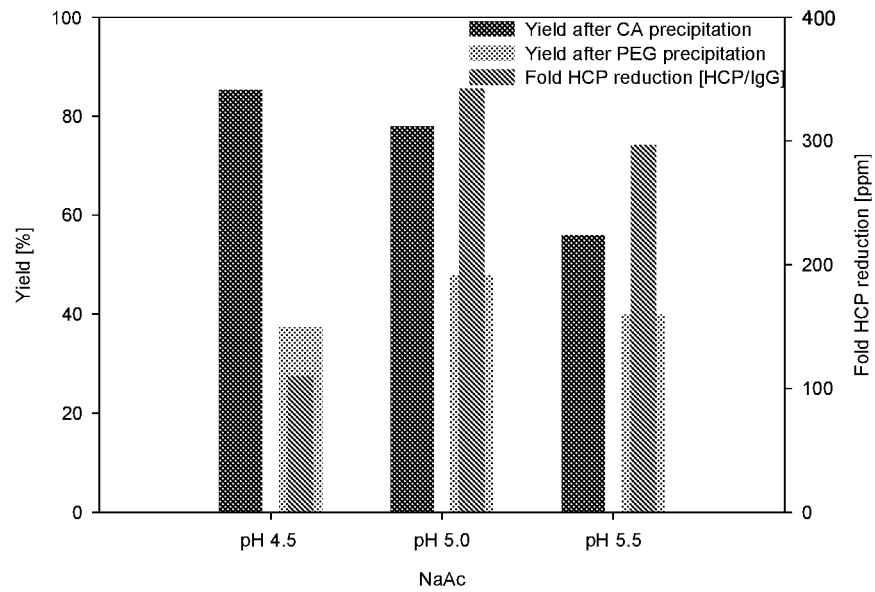
B. B07
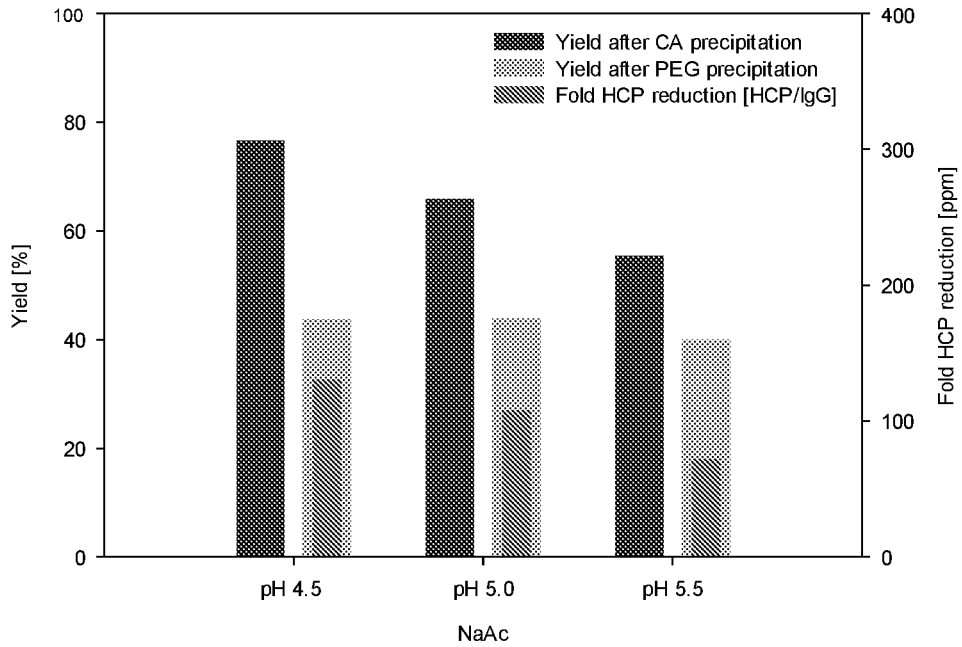

FIGURE 10
A. B03
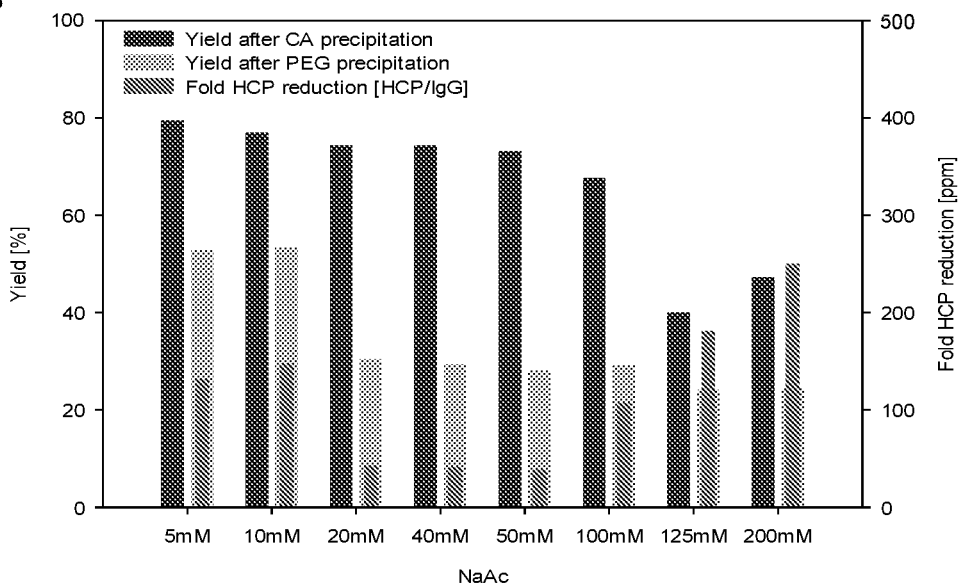
B. B07
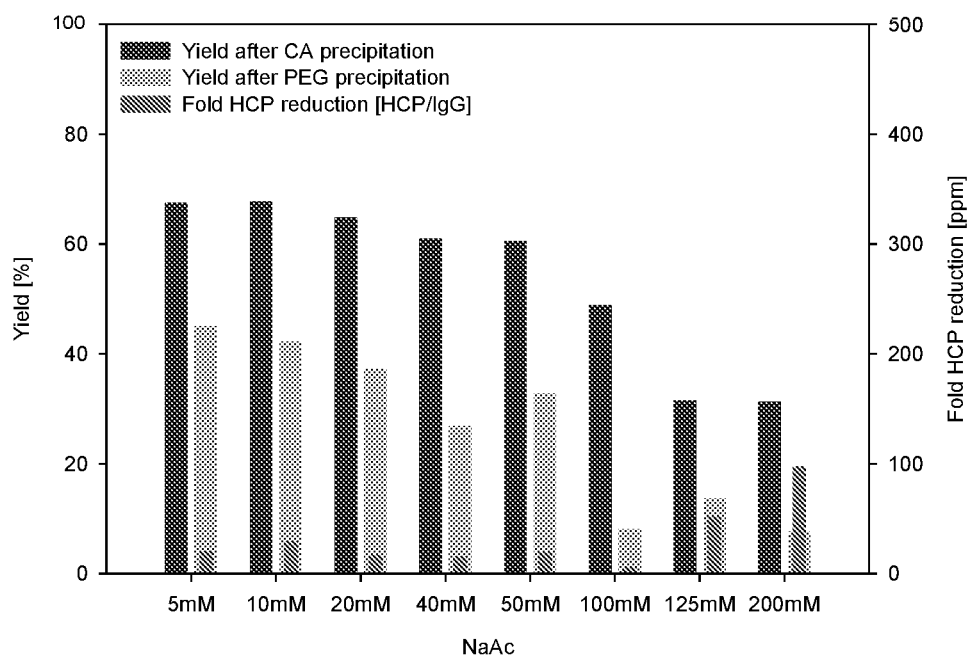

FIGURE 11
A. B03
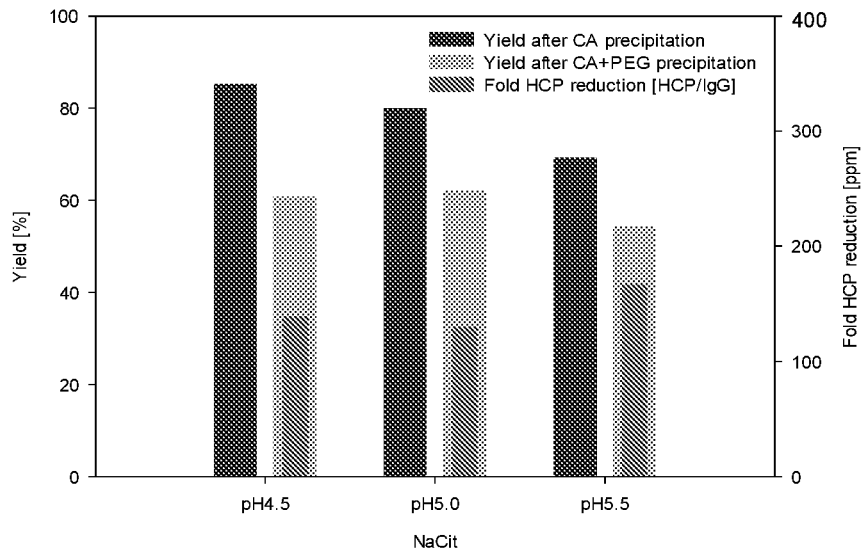
B. B07
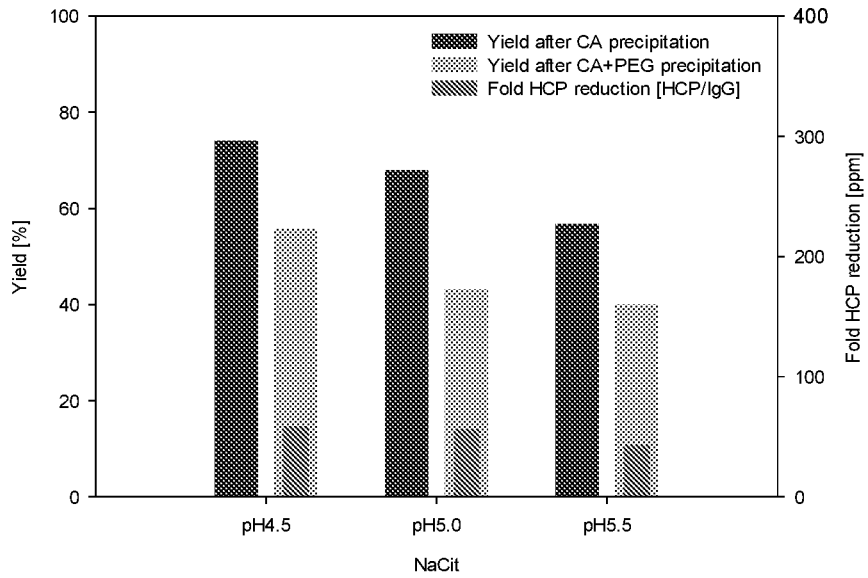

FIGURE 12
A. B03
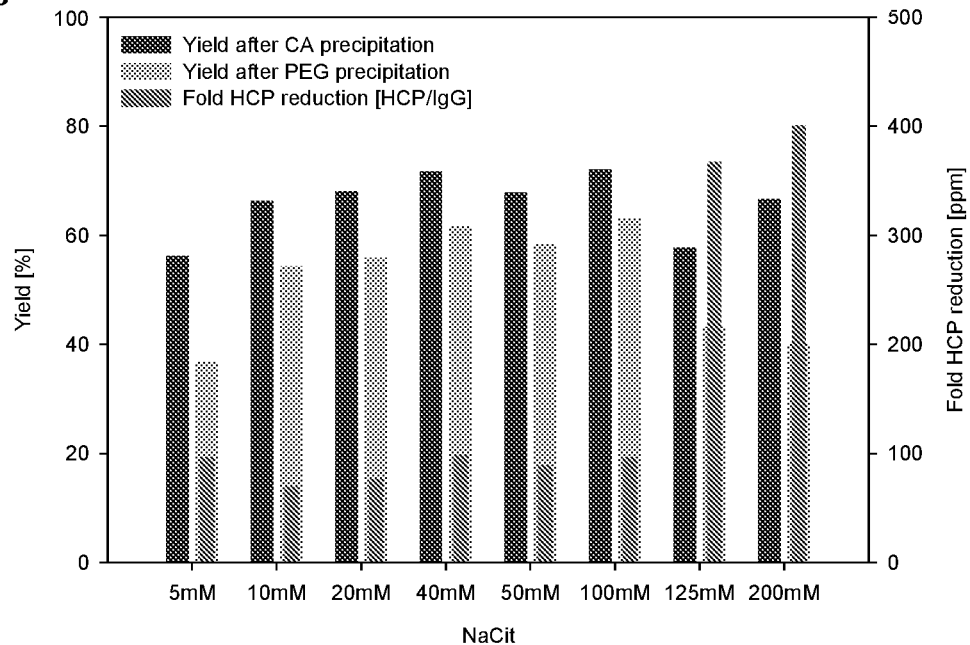
B. B07
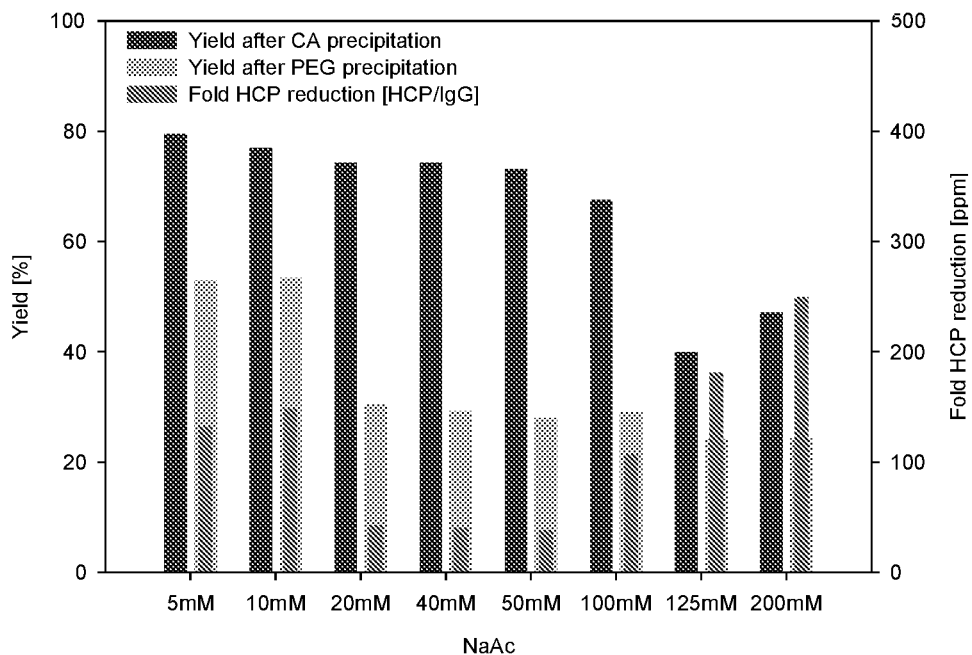

FIGURE 13
A. B03
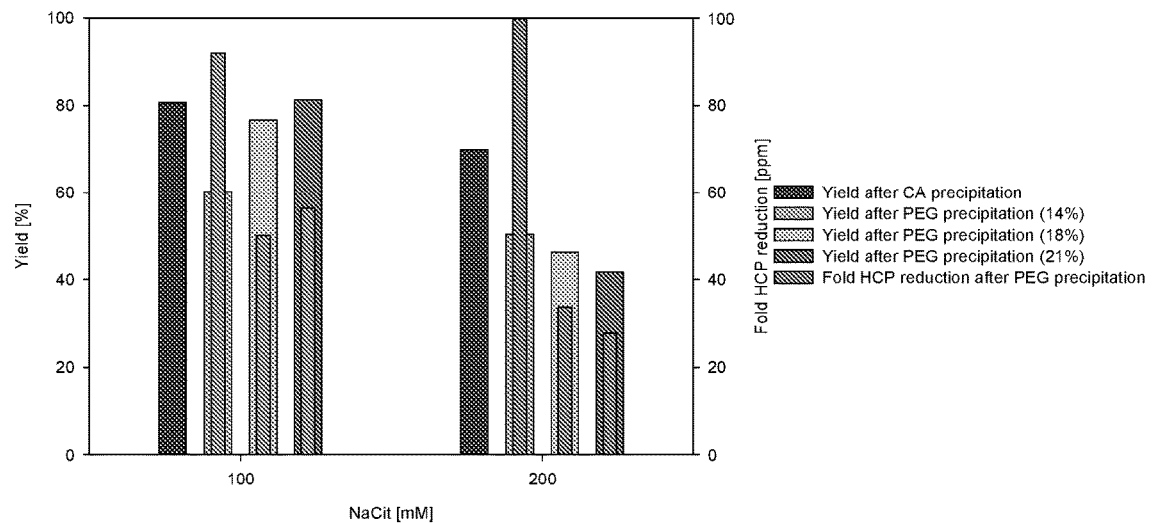
B. B07
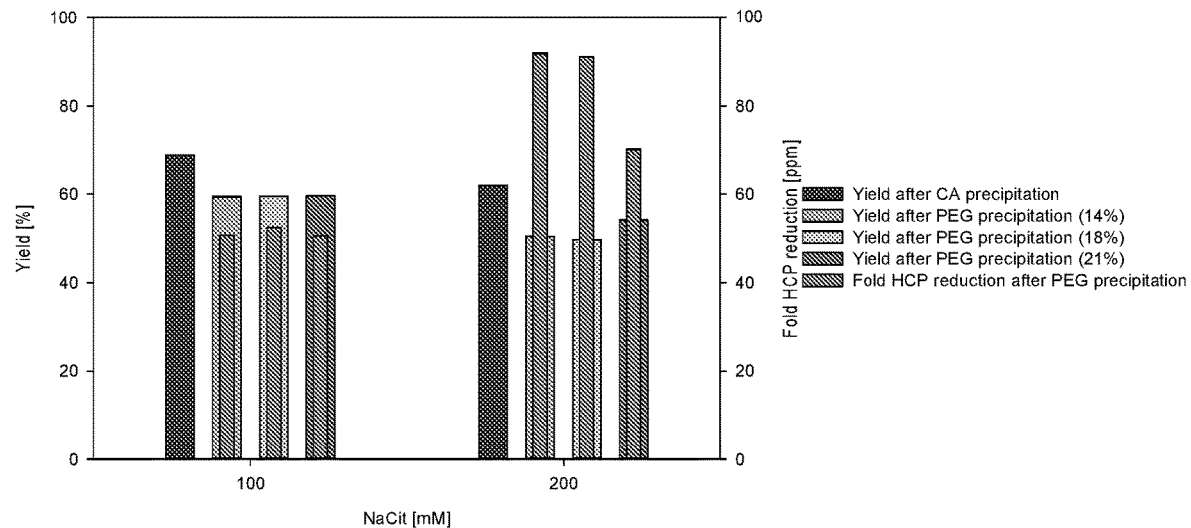

FIGURE 14
A. B03
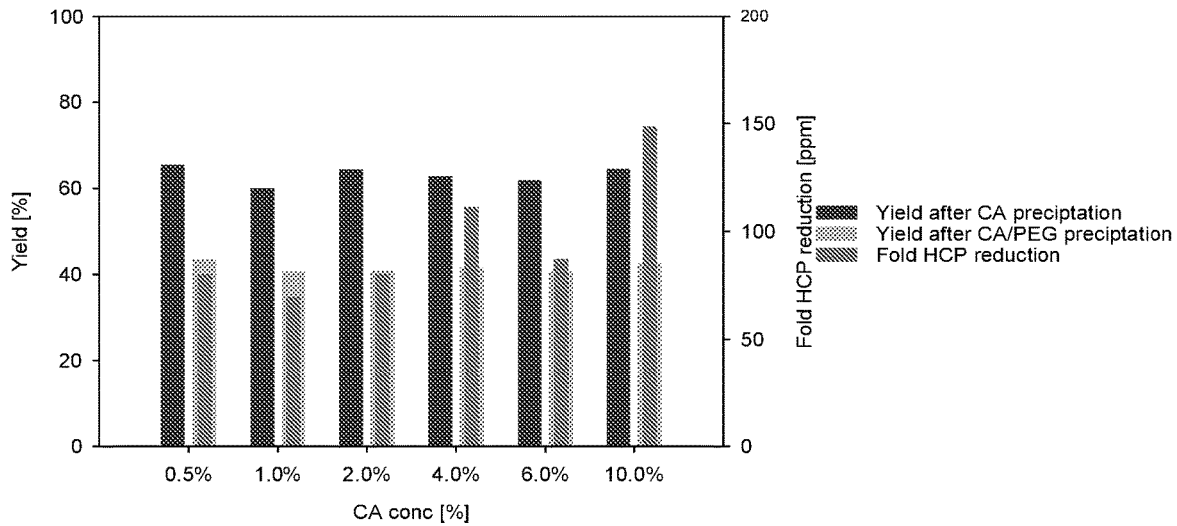
B. B07
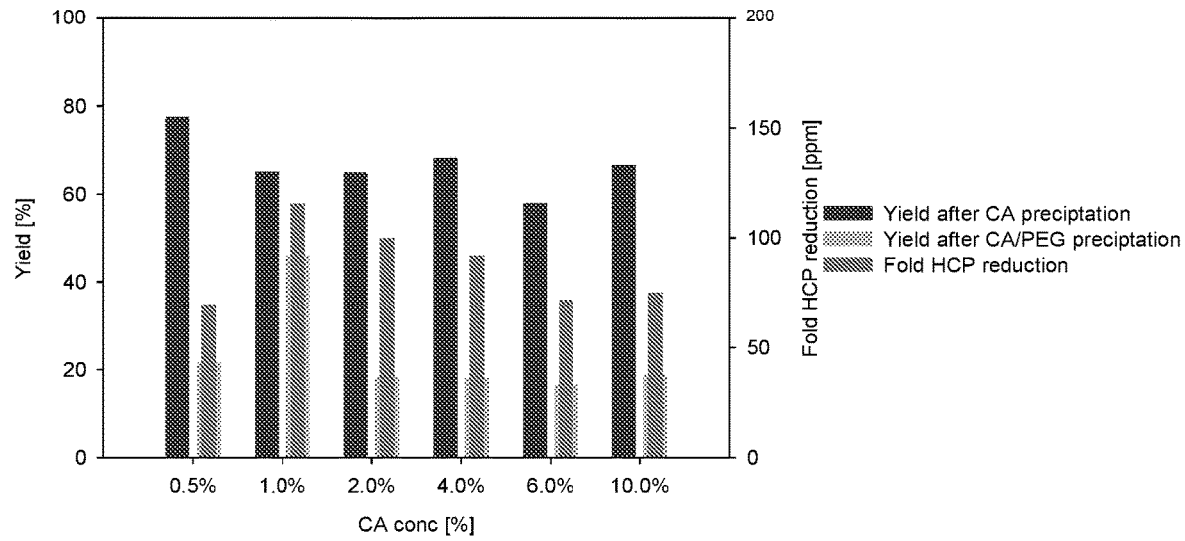

FIGURE 15
A. B03
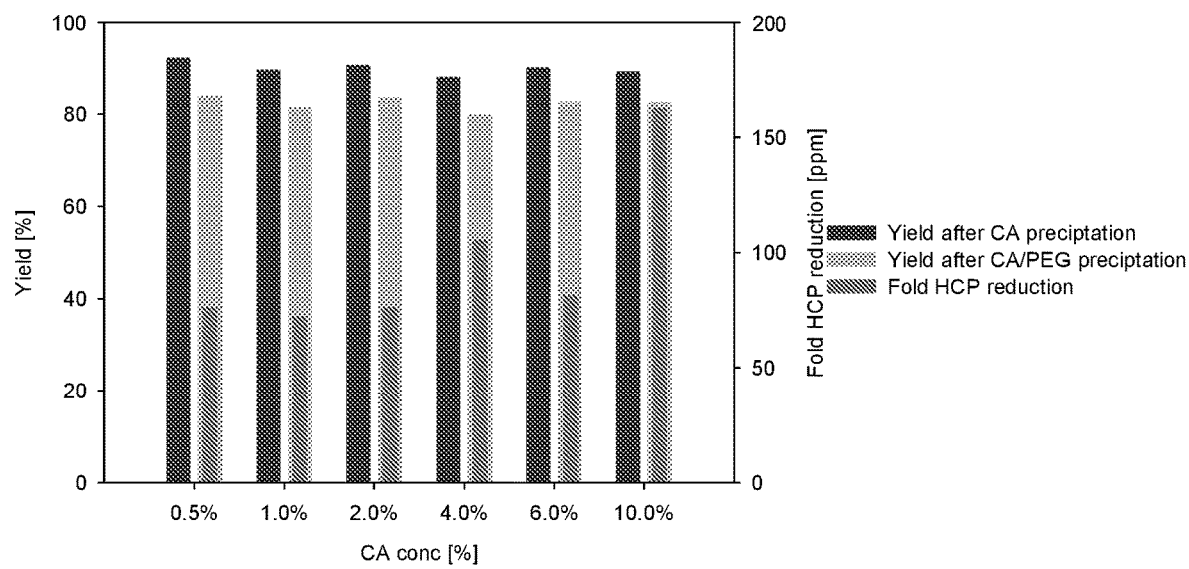
B. B07
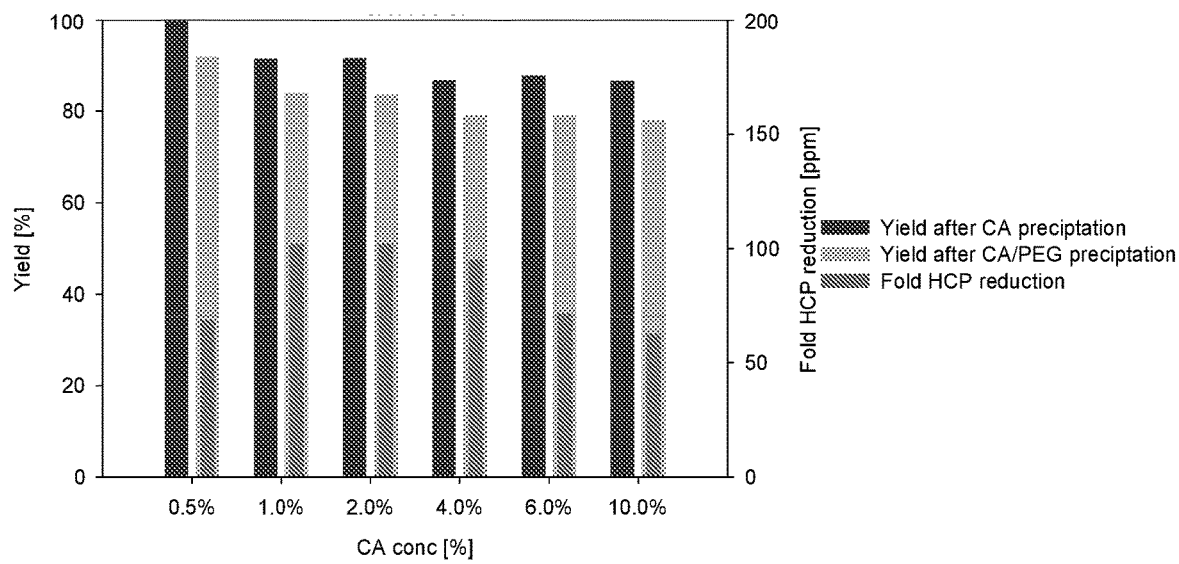

FIGURE 16
A. B03
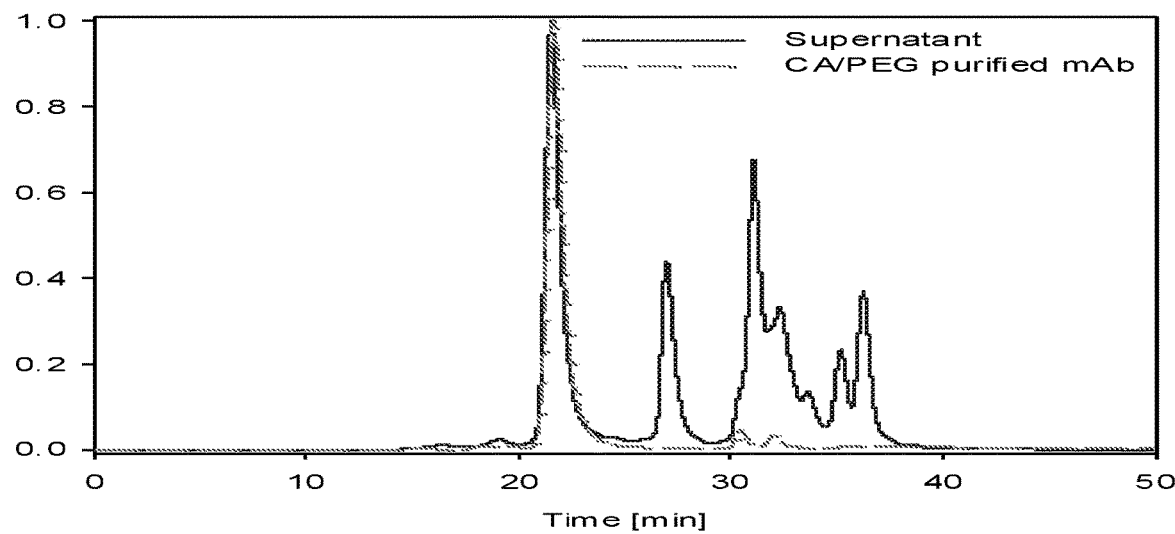
B. B07
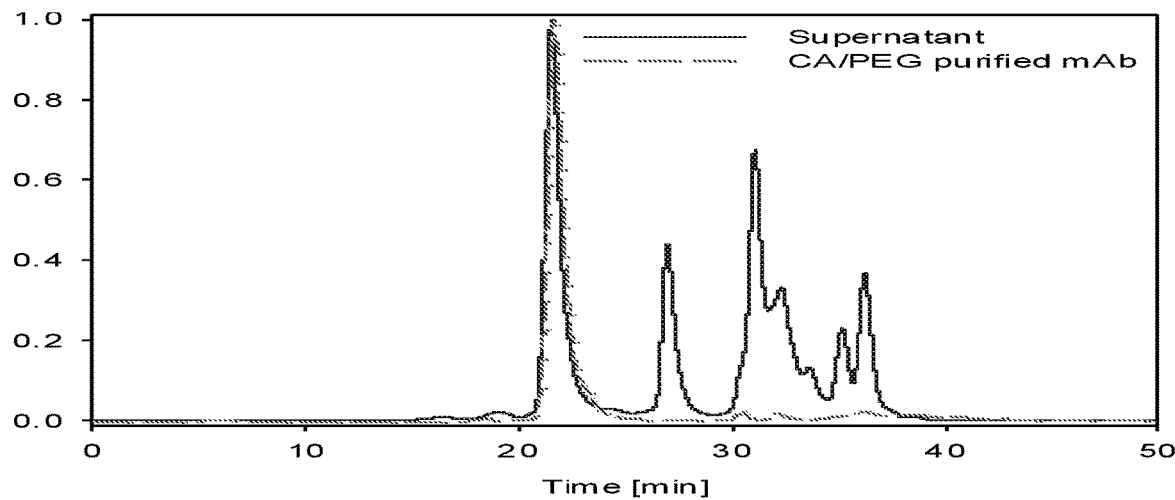

FIGURE 17A-B
A.
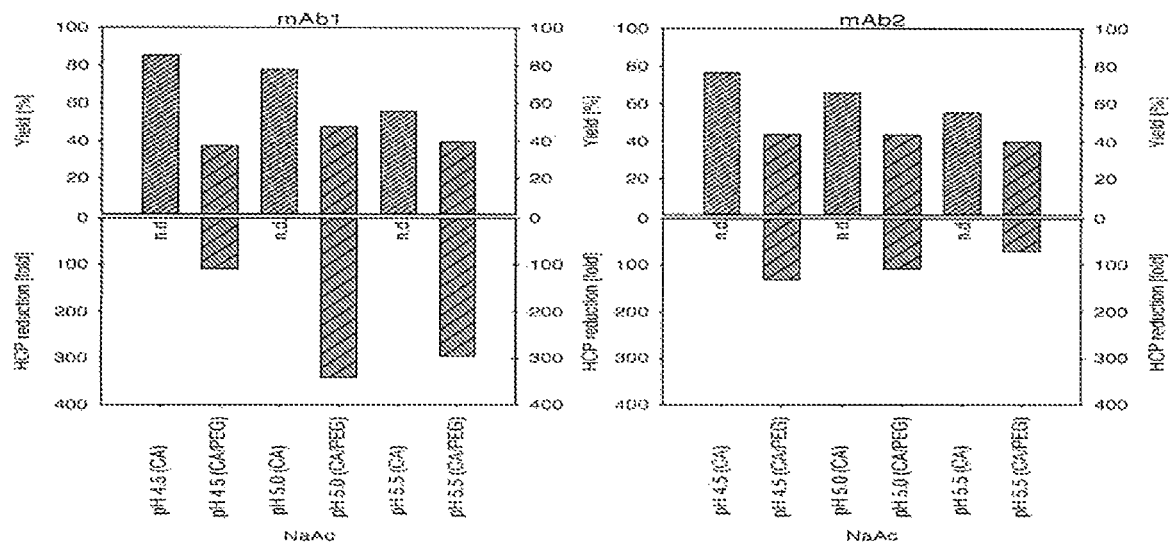
B.
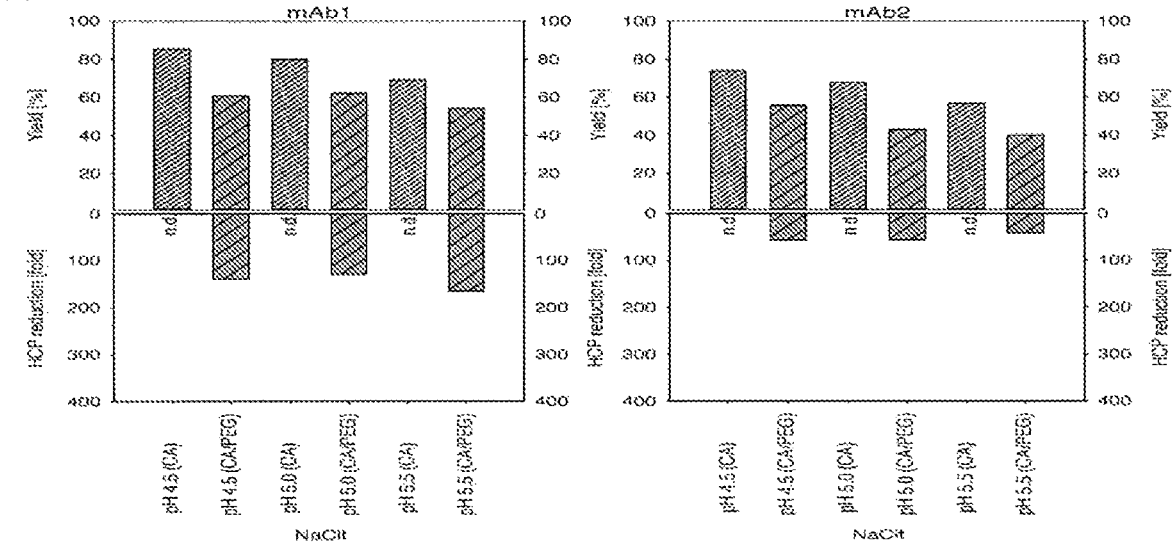

FIGURE 17C-D
C.
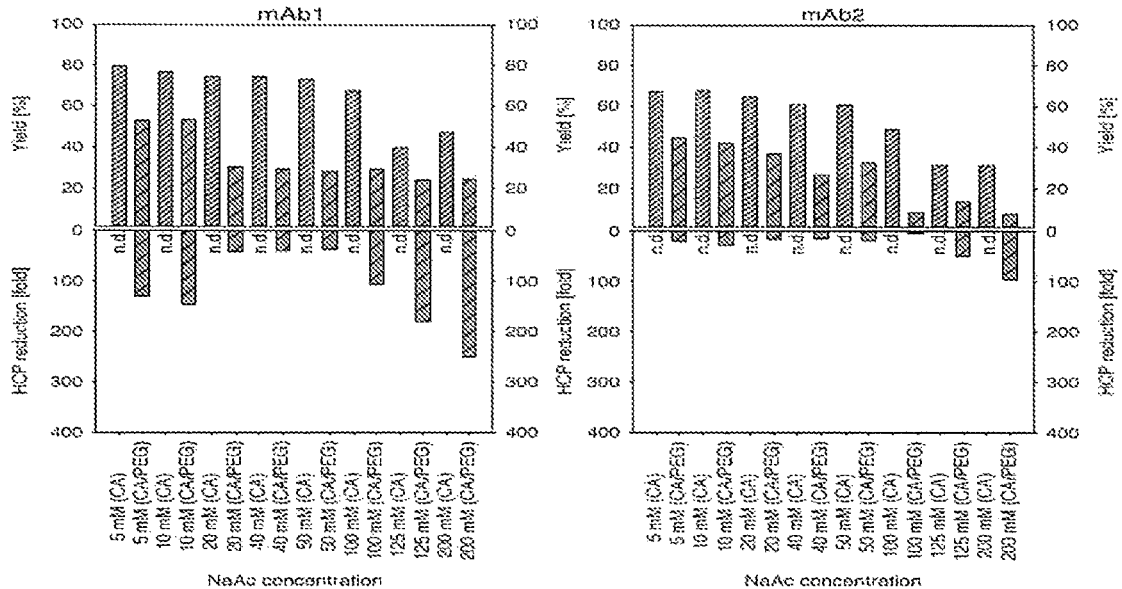
D.
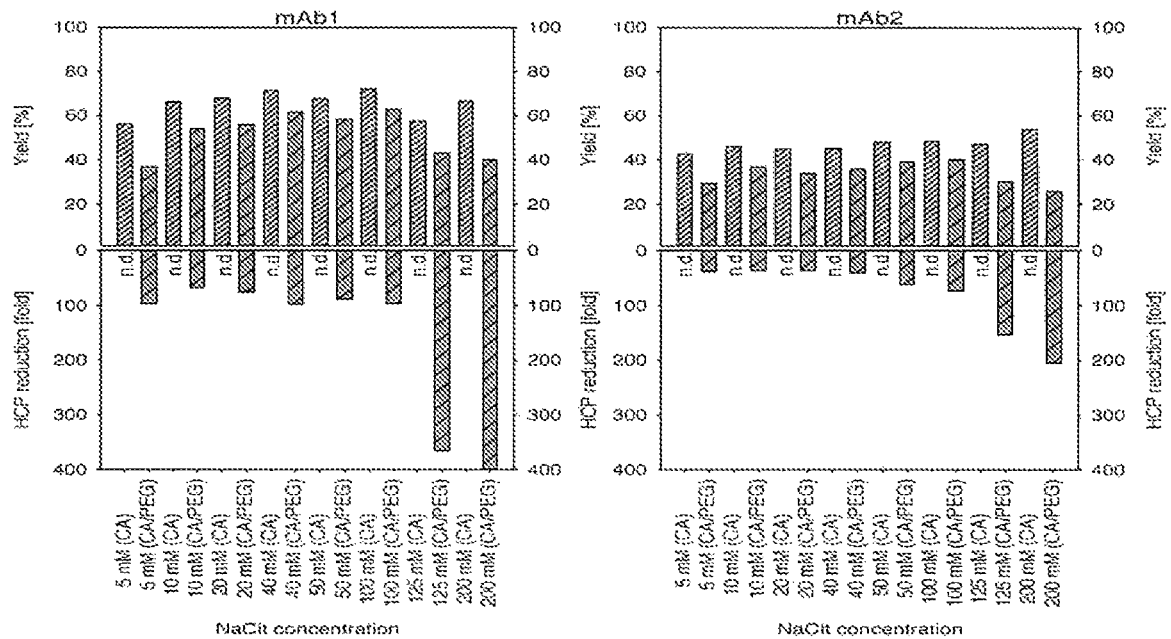

FIGURE 17E-F
E.
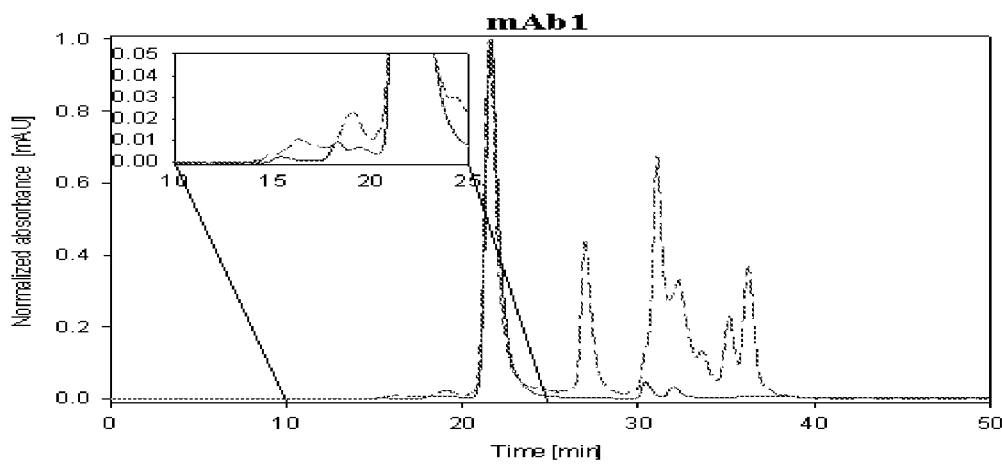
F.
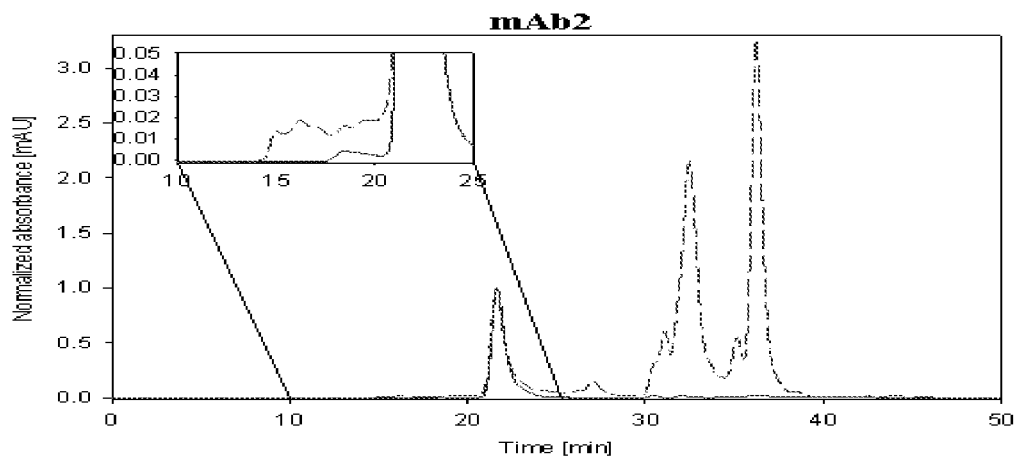

FIGURE 18
A.
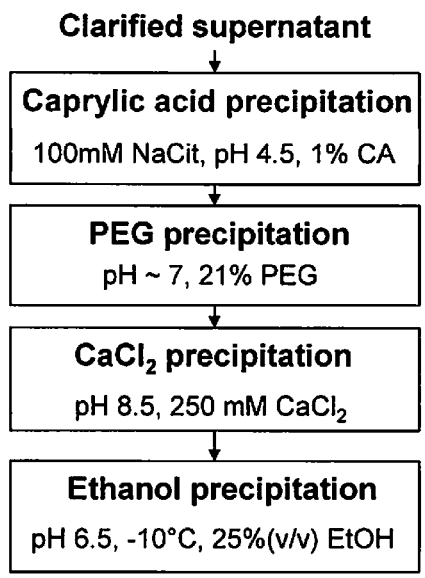
B.
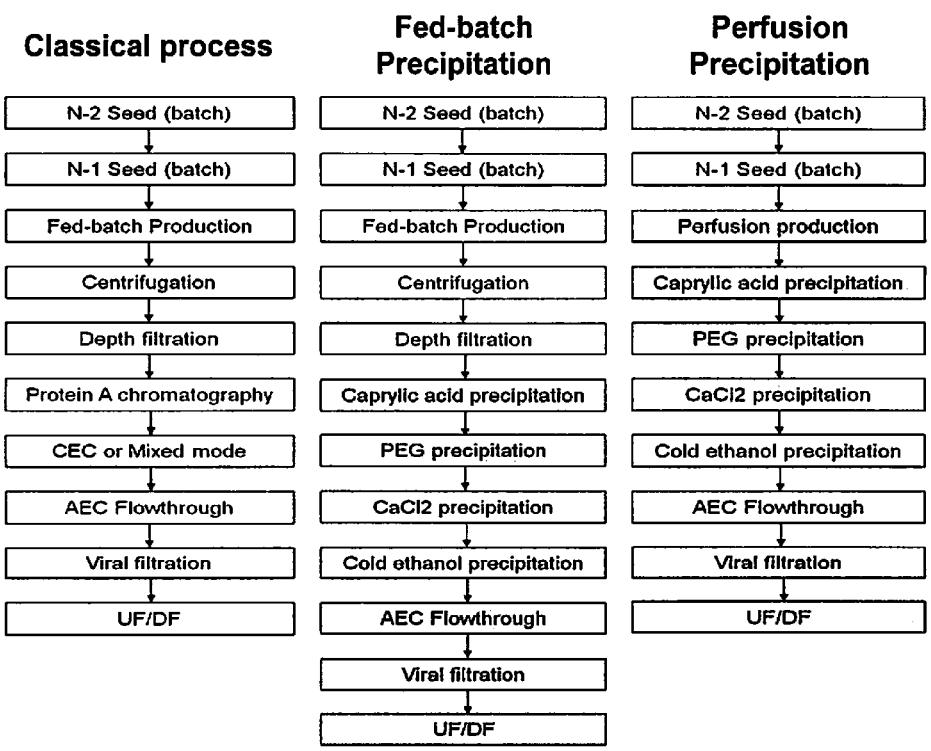

Tubular reactor for continuous mAb purification

PURIFICATION OF PROTEINS

RELATED APPLICATION

This application is a 35 U.S.C. § 371 national stage application of International Application No. PCT/IB2014/065412, filed Oct. 17, 2014, and claims priority to U.S. provisional application 61/892,975 filed Oct. 18, 2013.

FIELD OF THE DISCLOSURE

This application relates to methods for purification of proteins such as antibodies.

BACKGROUND OF THE DISCLOSURE

Precipitation of IgG (recombinant antibody) with a hydrophobic polymer (polyethylene glycol=PEG) is an alternative method to the conventional protein A affinity chromatography for purification of monoclonal antibodies. Protein precipitation with PEG was established by Polson (Polson et al. 1964). Atha and Ingham (Atha and Ingham 1981) showed that the concentration of precipitated protein increases with increasing PEG concentration and that the precipitation is also influenced by PEG size and pH value (Polson et al. 1964). It is assumed that the precipitation mechanism with polyethylene glycol is a volume exclusion reaction (Mahadevan and Hall 1990). PEG can be used to precipitate large proteins (e.g., host cell proteins (HCP)) as well as DNA. However, separation of IgG from DNA (as well as other larger proteins) with PEG as differences in molecular mass by a factor of about two is required to approach complete (e.g., 100%) separation (Lis and Schleif 1975). To obtain the required DNA and HCP clearance, PEG precipitation may be combined with another precipitation approach. Caprylic acid precipitation is a common way to separate venom out of horse plasma (Rojas et al. 1994). In several publications the precipitation parameter for caprylic acid precipitation are described (McKinney and Parkinson 1987; Mohanty and Elazhary 1989; Russo et al. 1983). Caprylic acid precipitation was combined with different purification methods like ammonium sulphate precipitation to purify human immunoglobulins (Perosa et al. 1990) or with ion-exchange chromatography to separate equine antivenom (Raweerith and Ratanabanangkoon 2003). Also, a CA precipitation of process-derived impurities out of CHO cell culture supernatant combined with an additional cation-exchange chromatographic step has also been performed (Wang et al. 2009).

Caprylic acid has also been used to precipitate non-immunoglobulin proteins from human plasma. The crude IgG present in the supernatant (which contained 26-29% of the total protein in terms of absorbance units or 78-87% of IgG by weight) was fractionated on DEAE-cellulose, to yield pure IgG as shown by disc electrophoresis, Immuno-electrophoresis and gel filtration. Pure IgG was free of plasmin and plasminogen and did not exhibit any fragmentation or aggregation during storage for periods up to 4 weeks at 40° C., and its anticomplementary activity was low. Antibodies to viral agents were recovered unchanged. (Habeeb, et al. Preparation of Human Immunoglobulin by Caprylic Acid Precipitation. Preparative Biochemistry, 14(1): 1-17 (1984)).

Parkkinen, et al. (Vax Sanguinis, 90: 97-104 (2006)) describe the isolation of pure, essentially polymer-free IgG from human Cohn fraction II+III by caprylic acid treatment to inactivate enveloped viruses and precipitate contaminating proteins and lipids, polyethylene glycol (PEG) precipitation of IgG, and final purification by anion-exchange chromatography. US 2007/0244305 A1 (Parkkinen, J.) described a similar process.

Bergmann-Leitner, et al. (Malaria J. 7: 129-139 (2008)) compares various immunuglobulin (Ig) procedures using immunized rabbit sera or malaria-exposed human sera as the Ig source. Procedures tested included enrichment of total Ig by caprylic acid depletion of serum proteins followed by ammonium sulfate precipitation (CA-AS). The CA-AS method was found to provide good yield without significant degradation. PEG precipitation was found to be optimal for isolating human Ig.

Vargas, et al. (Biotechnol. Prog., 28(4): 1005-1011 (2012)) describes the separation of human IgG from albumin as upper and lower phases by PEG precipitation. IgG present in the upper phase was then further isolated by caprylic acid precipitation and ion exchange chromatography.

U.S. Pat. No. 4,164,495 (Hansen, J.) describes methods for isolating immunoglobulins (Ig) using a polycondensed di or polyol, such as polyethylene glycol, in the presence of a mono or polyalkanoic acid having 4 to 12 carbon atoms, such as caprylic acid. Described therein is a method for isolating Ig from human blood plasma by first precipitating fibrinogen therefrom using PEG alone, isolating the precipitate comprising Ig, dissolving the same in sodium chloride solution, and admixing the solution with caprylic acid and PEG. The resulting precipitate is removed and the liquid phase precipitated with PEG alone to obtain "pure" Ig at a 60% yield.

U.S. Pat. No. 5,164,487 (Kothe, et al.) relates to methods for isolating "intravenously tolerable" Ig by treating a raw fraction containing IgG obtained by chromatography or Cohn processes and enriching the IgG using 0.4 to 1.5% octanoic acid (by volume) and chromatography (ion or cation exchanger or hydrophobic matrix). An "intravenously tolerable" preparation is described as one that may be administered to patients without side effects.

Steinbuch, et al. (Arch. Biochem. Biophys. 134: 279-284 (1969)) describes the use of caprylic acid to precipitate purified IgG (to 90% with caprylic acid/acetate buffer (pH 4.8)) and ion exchange cellulose and/or size exclusion chromatography (to remove IgA, ceruloplasmin and $\alpha_1$-acid-glycoprotein) from human serum. A similar procedure was used to isolate Ig from animal (horse, sheep, rabbit) serum.

McKinney (J. Immunol. Meth. 96: 271-8 (1987)) discloses a two-step procedure for isolating IgG from mammalian ascites fluid. The first step precipitates albumin and other non-IgG proteins with caprylic acid (octanoic acid) and the second precipitates IgG with ammonium sulfate (e.g., 80-90% recovery from rabbit serum).

U.S. Pat. No. 5,747,031 (Ruch, et al.) describes a method for isolating Ig from whey (e.g., made from hyperimmune milk) by co-precipitating lipids and non-Ig proteins simultaneously with a charged polymer (e.g., chitosan) and a fatty acid (e.g., caprylic acid). The resultant supernatant is then further treated by, for instance, diafiltration, to obtain isolated Ig (e.g., 66-79%).

WO 86/05099A1 (Steinbuch, et al.) relates to a process for isolating IgG4 from human plasma using a saturated fatty acid such as caprylic acid.

US 2002/177693AA (Lebing, et al.) describes a process for purifying antibodies from human plasma by preparing a composition comprising precipitated Ig, dissolving the Ig in a solution having a pH of 3.8 to 4.5, adding caprylate ions and increasing the pH to 5.0 to 5.2, and removing the precipitated proteins, lipids and caprylate by filtration. Caprylate is then added to the resultant solution, the temperature increased, and a filter aid introduced. The resultant precipitate is then removed by flow filtration. The solution is then passed through two anion exchange chromatography columns to produce Ig at >99% purity.

WO 2012/136172A1 (Segura Ruiz, et al.) describes a process for the production of injectable blood-derived protein materials by fractionating source material in a two-phase system including phenol, one phase being precipitated with caprylic acid and the other phase being processed by thermocoagulation.

Svendsen, et al. (Lab. Animal Sci. 45(1): 89-93 (1995)) compares the purification of antibodies from egg yolk by ammonium sulfate, PEG and caprylic acid, respectively. Ammonium sulfate was determined to provide the best purity and yield, and caprylic acid was found not to yield any purified antibodies.

Tscheliessnig, et al. (J. Chromatography, 1216: 7851-7864 (2009)) describes a two-step purification process for IgM (from hybridomas) using PEG and anion-exchange chromatography. Purity ranged from 46% to >95% with yields of 28-84%.

Knevelman, et al. (Biotechnol. Prog. 26: 697-705 (2010)) describes rapid PEG-based precipitation of IgG4 from cell culture media. Maximum yield and purity were determined to result from the use of between 10-18% PEG (w/v).

Kuczewski, et al. (Biopharm. Int., Supp., pp. 20-28 (March 2010)) described PEG-based precipitation of monoclonal antibodies from clarified cell culture media in yields of approximately 90% and reduced host cell protein (HCP) content by a factor of seven. Antibody was captured by cation exchange chromatography. Use of PEG-3350 was found to provide higher recovery but less HCP reduction. PEG-6000 was found to better reduce HCP but result in a lower yield. PEG-3350 at 14% (pH 8.5) was selected as the optimal condition.

Gibson, et al. (J. Pharm. Sci. 100(3): 1009-1021 (2011)) relates to the use of PEG with citrate, acetate, histidine or phosphate buffers across various pH values to test the solubility of IgG1 mAb produced by a CHO cell or murine cell line (each providing different glycosylation patterns to the mAb). These comparisons were made to identify strategies for use in high-throughput analysis of mAb preparations.

There is a need in the art for improved methods for isolating proteins such as antibodies from cell culture supernatants. This disclosure provides such improved methods.

BRIEF DESCRIPTION OF THE DRAWINGS

FIG. 4. SEC (BIO-SEC 3, Agilent) chromatogram comparison of B03 (panel A) and B07 (panel B) supernatants (supernatant (SN) at pH 4.5 and SN after CA precipitation at ph 4.5).
FIG. 5. Yield of B03 and B07 after CA precipitation (1% CA) in presence of different NaAc salt concentrations at pH 5.5 and 40 rpm mixing speed; compared to cell culture supernatant (panel A) or pH adjusted cell culture supernatant (panel B).
FIG. 7. Yield (BIO-SEC 3, Agilent) and HCP (HCP-ELISA, Cygnus) of mAbs after CA and CA/PEG precipitation at different pH values (panel A: B03; panel B: B07).
FIG. 8. Yield (BIO-SEC 3, Agilent) improvement with increased PEG concentration for mAb precipitations (panel A: B03; panel B: B07).
FIG. 9. Yield (BIO-SEC 3, Agilent) of after CA (brown bar) and CA/PEG (green bar) precipitation and purity (HCP-ELISA, Cygnus) after CA/PEG precipitation (blue bar) at different pH values (panel A: B03; panel B: B07).
FIG. 10. Yield (BIO-SEC 3, Agilent) of mAbs after CA (brown bar) and CA/PEG (green bar) precipitation and purity (HCP-ELISA, Cygnus) after CA/PEG precipitation (blue bar) at different NaAc buffer concentrations (panel A: B03; panel B: B07).
FIG. 11. Yield (BIO-SEC 3, Agilent) of mAbs after CA (brown bar) and CA/PEG (green bar) precipitation and purity (HCP-ELISA, Cygnus) after CA/PEG precipitation (blue bar) at different pH values (panel A: B03; panel B: B07).
FIG. 12. Yield and fold-HCP reduction after CA and PEG precipitation (panel A: B03; panel B: B07).
FIG. 13. Yield (BIO-SEC 3, Agilent) of mAb after CA (brown bar) and CA/PEG (green bar) precipitation and purity (HCP-ELISA, Cygnus) after CA/PEG precipitation (blue bar) at 100 and 200 mM NaCit E: yield and purity following CA/PEG precipitation (mAb 1).
FIG. 14. Yield (BIO-SEC 3, Agilent) of mAb after CA (brown bar) and CA/PEG (green bar) precipitation and purity (HCP-ELISA, Cygnus) after CA/PEG precipitation (blue bar) at different CA concentrations in a NaCit buffer system (panel A: B03; panel B: B07).
FIG. 15. Yield (protein A affinity chromatography) of mAbs after CA (brown bar) and CA/PEG (green bar) precipitation and purity (HCP-ELISA, Cygnus) after CA/PEG precipitation (blue bar) at different CA concentrations in a NaCit buffer system (panel A: B03; panel B: B07).
FIG. 16. Comparison (SEC TSK3000 SWXL, Tosho, 280 nm) of CA/PEG precipitation purified mAbs and cell culture supernatants (panel A: B03; panel B: B07).
FIG. 17. Precipitation data (A: sodium acetate (NaAc); B: sodium citrate (NaCit); C: NaAc screening; D: NaCit screening; E: yield and purity following CA/PEG precipitation (mAb 1); F: yield and purity following CA/PEG precipitation (mAb 2).
FIG. 18A-B. Exemplary processes combining caprylic acid precipitation, PEG precipitation, $CaCl_2$ precipitation, and ethanol precipitation.

SUMMARY OF THE DISCLOSURE

Figure 1:
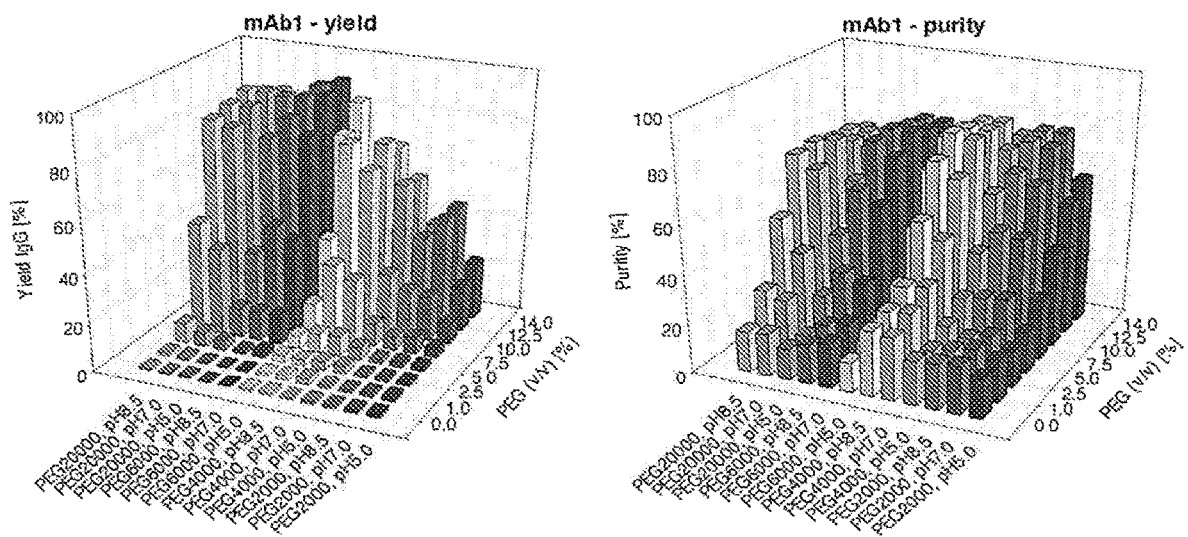
FIG. 1. PEG precipitation analysis.

In some embodiments, this disclosure relates to methods for isolating a protein of interest from nucleic acids and other host cell proteins present in cell culture supernatant comprising said protein, comprising combining said cell culture supernatant with 10-14% polyethylene glycol (PEG (e.g., PEG2000, PEG4000, PEG6000 and PEG20000)) (e.g., about 14% or about 21%) at a pH of 5.0-8.5. In some embodiments, 14% PEG6000 is used. In some embodiments, these methods may comprise first precipitating nucleic acids and protein impurities using calcium chloride. In certain embodiments, these methods may comprise precipitating host cell proteins using a fatty acid (e.g., caprylic acid). In some embodiments, about 5 to about 200 mM or 0.1 to 10% fatty acid (e.g., caprylic acid) may be used and/or the pH may be between about 4.0 and about 6.0 (e.g., pH 4.5).

In some embodiments, such preparations may alternatively and/or also treated using calcium chloride (250 mM $CaCl_2$, pH 8.5) to precipitate impurities (e.g., DNA). The protein of interest may be isolated using any combination of methods such as precipitation of impurities using caprylic acid and/or calcium chloride, precipitation of the protein of interest using a polymer (e.g., PEG), and further precipitation (e.g., washing) using cold ethanol in any order where, however, precipitation in the presence of ethanol is typically performed last. In some embodiments, antibody may be isolated by precipitating impurities using caprylic acid, precipitating the protein of interest using a polymer (e.g., PEG), resolubilizing the protein of interest and precipitating impurities from that composition, removing such impurities, and precipitating (e.g., washing) the isolated antibodies using cold ethanol. In any of such methods, the protein of interest may be an antibody. In addition, these methods may be completed (e.g., the protein of interest is purified at a desired yield (e.g., about 80% or more) to a desired level (e.g., about 95% or higher purity) without using chromatography.

In some embodiments, this disclosure relates to methods for isolating immunoglobulin G (IgG) from cell culture supernatant by: (a) precipitating host cell contaminants (e.g., directly) from cell culture supernatant using at least one fatty acid (e.g., caprylic acid) in a buffer (e.g., citrate such as sodium citrate) to produce a secondary supernatant comprising immunoglobulin; and, (b) precipitating the IgG from the secondary supernatant using at least one hydrophilic polymer (e.g., polyethylene glycol (PEG)), optionally including at least one salt; wherein the IgG is purified to at least about 95%; the yield is at least about 80%. Typically, these methods do not include the use of chromatography. In certain embodiments, the concentration of caprylic acid used during step (a) may be from about 0.1% to about 10% (e.g., 1%) and/or about 5 mM to about 200 mM. In some embodiments, the pH used in step (a) may be about 4.0 to about 6.0 (e.g., about pH 4.5). In step (b), the concentration of PEG may be about 10% to about 30% (e.g., about 14% or about 21%); the pH during precipitation in step b) may be about 5 to about 8.5; and the temperature may be about 4° C. to about 35° C. In certain embodiments, the step b) may be complete after about 15 minutes and/or equilibrium is reached after about 30 to about 60 minutes. In some embodiments, at least one additional precipitation procedure (e.g., cold ethanol precipitation) follows step b). In addition, these methods may be completed (e.g., the antibody is purified at a desired yield (e.g., about 80% or more) to a desired level (e.g., about 95% or higher purity) without using chromatography.

In some embodiments, this disclosure also provides an apparatus and methods for continuous production of preparations comprising a substantially isolated protein of interest (e.g., an antibody). The apparatus may be, for instance, a two-step precipitation reactor (e.g., FIG. 18). In some embodiments, the reactor provides about a two liter volume and/or a suitable flow rate (e.g., 20 ml/min). The apparatus may comprise tubing (e.g., 5 mm diameter silicon tubes), magnetic valves, filter units and the like. The apparatus may also be configured such that the first and second precipitation reactions may be run independent of one another.

Other embodiments will be apparent from the disclosure provided herein.

DETAILED DESCRIPTION

As described briefly above and in more detail below, this disclosure relates to methods that solve problems typically encountered during the purification of proteins such as antibodies (e.g., monoclonal antibodies). The methods described herein may be surprisingly used to provide purified antibodies preparations from compositions comprising antibodies, other proteins, and/or nucleic acids, among other components. In some embodiments, the methods described herein provide for the production of highly pure antibodies (e.g., 95% or higher) in high yield (e.g., 80% or more) directly from cell-free culture supernatant.

As described above and in the claims, this disclosure relates to methods for isolating a protein of interest from nucleic acids and other host cell proteins present in cell culture supernatant (which may be a cell-free culture supernatant) comprising said protein using polyethylene glycol (PEG). In some embodiments, the methods comprise combining such a cell culture supernatant with a first precipitating agent (e.g., calcium chloride and/or a fatty acid such as caprylic acid) to remove precipitated proteins and/or other components to produce a secondary cell culture supernatant (e.g., which still comprises the protein of interest), and introducing a precipitating polymer (e.g., polyethylene glycol (PEG)) to precipitate the protein of interest (e.g., antibody) from the secondary cell culture supernatant. In some embodiments, calcium chloride may then be used to further remove impurities from the PEG-precipitated protein.

In certain embodiments, these methods may comprise precipitating cell culture components such as host cell proteins (HCPs) using one or more fatty acids (e.g., caprylic acid). In some embodiments, the fatty acid may be present in the precipitation mixture in an amount of from about 0.1% to about 10% (v/v) (e.g., about any of 0.1, 0.2, 0.3, 0.4, 0.5, 1.0, 1.5, 2.0, 2.5, 3.0. 3.5, 4.0, 4.5, 5.0, 5.5, 6.0, 6.5, 7.0, 7.5, 8.0, 8.5, 9.0, 9.5, or 10.0%) and/or about 5 to about 250 mM fatty acid (e.g., about any of 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 mM) may be used. A pH of about 4-6 (e.g., between about 4.5 and about 5.5, or about any of 4.1, 4.2, 4.3, 4.4, 4.5, 4.6, 4.7, 4.8, 4.9, 5.0. 5.1, 5.2, 5.3, 5.4, 5.5, 5.6, 5.7, 5.8, 5.9 or 6.0). The fatty acid may also be used with or without a salt (e.g., sodium acetate or sodium citrate (e.g., 0.1-200 mM of either salt such as about any of 0.1, 0.2, 0.3, 0.4, 0.5, 0.6, 0.7, 0.8, 0.9, 1.0, 1, 5, 10, 20, 30, 40, 50, 60, 70, 80, 90, 100, 110, 120, 130, 140, 150, 160, 170, 180, 190 or 200 mM). Precipitation may be carried out for a suitable amount of time such as, for instance, five to 90 minutes (e.g., about any of 5, 6, 7, 8, 9, 10, 11, 12, 13, 14, 15, 20, 25, 30, 35, 40, 45, 50, 55, 60, 65, 70, 75, 80, 85, or 90 minutes). Suitable temperatures for such reactions may be, for instance, about 4° C. to about 35° C. An exemplary method may comprise the step of preparing cell culture supernatant comprising about 1% caprylic acid, adjusting the pH 4.5 of the cell culture supernatant/caprylic acid using a sodium acetate or sodium citrate preparation (e.g., present at about 10-300 mM, such as about any of 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 mM), and mixing these components for about ten minutes at room temperature (e.g., about 25° C.). The precipitants may then be removed from the cell culture supernatant to produce a secondary cell culture supernatant.

The secondary cell culture supernatant may then be treated with a polymer to precipitate the protein(s) of interest (e.g., antibody). A suitable polymer is polyethylene glycol (PEG). Suitable PEG polymers may include but are not limited to, for instance, PEG2000, PEG4000, PEG6000 and PEG20000. Precipitation may be accomplished by introducing PEG into the secondary cell culture supernatant in an amount of about 5-30% (e.g., about 10-21%, or about 10-14%, or about any of 5, 6, 7, 8, 9, 10, 11, 12, 13, 14, 15, 16, 17, 18, 19, 20, 21, 22, 23, 24, 25, 26, 27, 28, 29 or 30%). A suitable pH of the mixture may be about any of 4-9 (e.g., about 5.0-8.5, or about 4, 4.5, 5, 5.5, 6, 6.5, 7, 7.5, 8, 8.5, or 9). The pH used in these methods is typically selected without consideration of the pI of the protein of interest. Precipitation may be carried out for a suitable amount of time such as, for instance, five to 90 minutes (e.g., about any of 5, 6, 7, 8, 9, 10, 11, 12, 13, 14, 15, 20, 25, 30, 35, 40, 45, 50, 55, 60, 65, 70, 75, 80, 85, or 90 minutes). Suitable temperatures for such reactions may be, for instance, about 4° C. to about 35° C. An exemplary method may comprise the step of preparing cell culture supernatant comprising about 14% or about 21% PEG (e.g., PEG6000), at a pH of between about 5 and about 8.5 (e.g., independent of protein of interest pI), allowing precipitation to occur for at least about ten to 15-60 minutes at an appropriate temperature (e.g., about room temperature or about 25° C.), and isolating the precipitate which contains the protein of interest. The protein of interest may then be isolated and/or resuspended in an appropriate buffer and/or solution to produce a composition comprising the protein of interest. In some embodiments, these methods may comprise precipitating nucleic acids and protein impurities from that composition using calcium chloride. In some such embodiments, a composition comprising the protein of interest may be treated with calcium chloride ($CaCl_2$) (e.g., about any of 10-400 mM, such as about any of 10, 25, 50, 75, 100, 125, 150, 175, 200, 225, 250, 275, 300, 325, 350 or 400 mM) at an appropriate pH (e.g., any of about 6 to about 9, such as about any of 6, 6.5, 7, 7.5, 8, 8.5 or 9) to precipitate such impurities (e.g., DNA). Typically, calcium chloride precipitation may be performed after caprylic acid precipitation and PEG precipitation but before ethanol precipitation (e.g., FIG. 18). However, any of these precipitation steps may be used before, after, or at the same time as any other precipitation step as may be determined by one of ordinary skill in the art.

These methods may be considered complete once the protein of interest is purified at a desired yield (e.g., about 80% or more) and/or to a desired level (e.g., about 95% or higher purity) without using chromatography. The yield may, of course, be higher or lower than 80% (e.g., about any of 50, 55, 60, 65, 70, 75, 80, 85, 90, 95, 96, 97, 98, 99, 99.5, 99.9 or 100%). The level of purity may also be higher or lower than 95% (e.g., about any of 50, 55, 60, 65, 70, 75, 80, 85, 90, 95, 96, 97, 98, 99, 99.5, 99.9 or 100%). Purity may also be defined with reference to the amount of host cell proteins (HCPs) that are removed from the cell culture supernatant, which may be expressed as "fold-HCP reduction" or a similar term (e.g., about any of 10, 25, 50, 100, 150, 200, 250, 300, 350, 400, 450, or 500-fold HCP reduction). These measurements may be combined in any desired form (e.g., yield/purity, yield/fold-HCP reduction, yield/fold-HCP reduction/purity, and/or purity/fold-HCP reduction). The yield, purity and/or HCP levels may be determined using any of the tools available to those of ordinary skill in the art including but not limited to chromatography (e.g., size exclusion (SEC), protein A) and/or enzyme-linked immunosorbant assay (ELISA). Other measurements of yield and/or purity and methods for making such determinations are available to those of ordinary skill in the art and may be appropriate for use here, as will be appreciated by those of ordinary skill in the art.

In some embodiments, this disclosure relates to methods for isolating a protein of interest which is an antibody such as immunoglobulin G (IgG) from cell culture supernatant by: (a) precipitating host cell contaminants (e.g., directly) from cell culture supernatant using at least one fatty acid (e.g., caprylic acid) in a buffer (e.g., citrate such as sodium citrate) to produce a secondary supernatant comprising immunoglobulin; (b) precipitating the IgG from the secondary supernatant using at least one hydrophilic polymer (e.g., polyethylene glycol (PEG)), optionally including at least one salt; and, optionally, (c) precipitating impurities from a composition comprising the antibodies precipitated in step (b); wherein the IgG is purified to at least about 95%; the yield is at least about 80%. Typically, these methods do not include the use of chromatography. In certain embodiments, the concentration of caprylic acid used during step (a) may be from about 0.5% to about 10% (v/v) and/or about 5 mM to about 200 mM. In some embodiments, the pH used in step (a) may be about 4.5 to about 5.5 (e.g., about 4.5). In step (b), a suitable concentration of PEG may be as described above (e.g., about 14% or about 21%); the pH during precipitation in step b) may be about 5 to about 8.5 (e.g., about pH 7); and the temperature may be about 4° C. to about 35° C. The amount of calcium chloride ($CaCl_2$) used in optional step (c) may be any appropriate amount such as, for instance, 250 mM. In certain embodiments, the step b) may be complete after about 15 minutes and/or equilibrium is reached after about 30 to about 60 minutes. In some embodiments, at least one additional precipitation procedure (e.g., cold ethanol precipitation) follows step b). In addition, these methods may be completed (e.g., the antibody is purified at a desired yield (e.g., about 80% or more) to a desired level (e.g., about 95% or higher purity) without using chromatography.

In some embodiments, this disclosure also provides an apparatus and methods for continuous production of preparations comprising a substantially isolated protein of interest (e.g., an antibody). The apparatus may be, for instance, a two-step precipitation reactor (e.g., FIG. 18). In some embodiments, the reactor provides about a two liter volume and/or a suitable flow rate (e.g., 20 ml/min). The apparatus may comprise tubing (e.g., 5 mm diameter silicon tubes), magnetic valves, filter units and the like. The apparatus may also be configured such that the first and second precipitation reactions (or additional precipitation steps) may be run independent of one another.

The phrase "directly from cell culture supernatant" typically means that the culture supernatant (e.g., cell-free culture supernatant) is not treated (e.g., no "pre-treatment"), other than being collected for processing, such that the ratio of other components (e.g., non-antibody components such as host cell proteins (HCP)) to the protein of interest (e.g., antibody) of the culture supernatant is not substantially altered prior to carrying out the methods described herein (e.g., the culture supernatant is not treated in a way that may be understood to separate and/or isolate HCP from immunoglobluin, and/or purify the immunoglobulin from HCP). Thus, for isolating an antibody, the methods described herein may begin with a cell-free culture supernatant of a hybridoma producing a monoclonal antibody to be isolated. It should be understood that other starting materials (e.g., ascites, a semi-purified, or purified preparation containing the antibody to be crystallized) may also be used. These methods may also be suitable for isolation of "purified" polyclonal antibodies from sera and the like. Regarding a cell-free culture supernatant, it may be used directly from culture or, in some embodiments, concentrated prior to processing. The cell-free culture supertant may be concentrated by a factor of, for example, any of about 2, 3, 4, 5, 6, 7, 8, 9, 10, 11, 12, 13, 14, 15, 16, 17, 18, 19 or 20 to provide a lesser volume and, therefore, a higher concentration of proteins (and other components) (e.g., 100 ml to 10 ml being a factor of 10, or 10:1). The protein concentration of the cell-free supernatant may be, for example, about 1-100 g/L, such as any of about 10 g/L, 25 g/L, or 50 g/L. Concentration may be achieved using any of several widely available technique such as, for example, centrifugation, ammonium sulphate concentration, spin centrifugation and/or ultrafiltration (e.g., Amicon Ultra-15 Centrifugal Filter Unit with Ultracel-10 membrane), as would be understood by one of ordinary skill in the art. These and other suitable starting materials would be understood by one of ordinary skill in the art.

Thus, this disclosure provides methods for purification of proteins such as antibodies using a fatty acid such as caprylic acid (CA) for separation of impurities (host cell proteins, dsDNA) and a hydrophilic polymer such as polyethylene glycol (PEG) for antibody precipitation. Impurities of cell culture supernatant may be separated from such proteins using caprylic acid and, in some embodiments, by adding sodium citrate 100 mM and adjusting pH to 4.5. In certain embodiments, precipitation may be substantially complete after approximately 30 to 60 minutes vigorous mixing. The protein may be precipitated by addition of PEG in the presence or absence of salts, at a suitable pH (e.g., between about 5 and 8.5 (independent of the protein pI)) at a suitable temperature (e.g., between about 4 to 35° C.). Precipitation may be almost complete after approximately 10-15 minutes; equilibrium may be reached after approximately 30 to 60 minutes. Supernatant may then be discarded and precipitate washed and/or resuspended for further purification using another agent such as calcium chloride, and then re-precipitated (e.g., washed). The ultimate precipitate can be dissolved in an appropriate buffer or lyophilized for storage. The process can be performed in a batch and continuous operation. The method is intended for purification of recombinant antibodies and fragments (probably also other recombinant proteins) at large scale as alternative to chromatographic processes. The process can be combined with other chromatographic or non-chromatographic steps. This method can be generically applied for the purification of recombinant antibodies, fragments and similar proteins.

In some embodiments, this disclosure provides methods for purifying proteins (e.g., recombinant antibody) with fatty acid(s) and hydrophilic polymers solution yielding a native protein separated from dsDNA, host cell proteins, and other impurities generated during production of the antibody. In certain embodiments, a method for precipitation of impurities/proteins (pI≤7) with a fatty acid (e.g., caprylic acid) (without increasing the working volume) and with sodium citrate instead of sodium acetate as main buffer component. Working volume is understood by those of ordinary skill in the art to be a very important issue in downstream processing methods as lower volumes may accelerate process speed and the footprint of equipment is reduced. In some embodiments, such advantages are recognized by the methods described herein.

In certain embodiments, this disclosure provides methods for precipitating proteins (e.g., antibodies) from cell culture or fermentation supernatant using a hydrophilic polymer solution (polyethylene glycol) without adding salt (sodium phosphate) and/or adjusting the pH to the antibody pI. The methods described herein also function independent of the culture supernatant conditions. Thus, conditioning steps are not required and this subsequently simplifies the process. Furthermore, the precipitation may be completed within 10 to 15 minutes. This disclosure also demonstrates a combination between a fatty acid precipitation of impurities and hydrophilic polymer precipitation of recombinant antibodies/similar proteins for reaching first capture step requirements.

In certain embodiments, caprylic acid precipitation, PEG precipitation and/or $CaCl_2$ precipitation may be combined into a single process (e.g., FIGS. 18A and 18B). In an exemplary embodiment, a clarified cell culture supernatant may be first precipitated using sodium citrate or sodium acetate and caprylic acid at a suitable pH as described herein (e.g., 100 mM sodium citrate (NaCit), pH 4.5, 1% caprylic acid) and the resulting precipitate removed to provide a secondary supernatant. Antibody may then be precipitated from the secondary supernatant using a suitable amount of PEG and at a suitable pH (e.g, PEG 21%, pH 7), isolated, and resuspended in an appropriate buffer. The isolated antibody may then be precipitated from this preparation using a suitable amount of calcium chloride at a suitable pH (e.g, 250 mM $CaCl_2$, pH 8.5). The precipitate may then be resuspended in an appropriate buffer and re-precipitated (e.g., washed) in ethanol (e.g., 25% (v/v), pH 6.5, −10° C.). An exemplary embodiment of this combined process and the results thereof is described in Example 5. The antibody isolated by such process may provide more desirable yield, purity, reduction in HCP as the other methods described herein. In some embodiments, ultrafiltration, diafiltration and/or ion exchange chromatography may be added as an additional step to further purify the antibody.

As mentioned above, in certain embodiments, the protein of interest may be an antibody. Exemplary antibodies may include, for instance, human antibodies (e.g., IgG (IgG1, IgG2, IgG3, IgG4), IgM, IgA (IgA1 and IgA2), IgD, and IgE), canine antibodies (e.g., IgGA, IgGB, IgGC, IgGD), chicken (e.g., IgA, IgD, IgE, IgG, IgM, IgY), goat antibodies (e.g., IgG), mouse antibodies (e.g., IgG, IgD, IgE, IgG, IgM), pig antibodies (e.g., IgG, IgD, IgE, IgG, IgM), rat antibodies (e.g., IgG, IgD, IgE, IgG, IgM) and/or fragments and/or derivatives thereof. A suitable, exemplary type of antibody may be, for instance, human IgG. Exemplary fragments and/or derivatives may include, for example, Fab, $F(ab')_2$, Fab' single chain antibody, Fv, single chain, mono-specific antibody, bi-specific antibody, tri-specific antibody, multi-valent antibody, chimeric antibody, canine-human chimeric antibody, canine-mouse chimeric antibody, antibody comprising a canine $F_c$, humanized antibody, human antibody, caninized, CDR-grafted antibody, shark antibody, nanobody (e.g., antibody consisting of a single monomeric variable domain), camelid antibody (e.g., antibodies members of the Camelidae family) microbody, intrabody (e.g., intracellular antibody), and/or de-fucosylated antibody and/or derivative thereof. Mimetics of binding agents and/or antibodies are also provided. Other types of antibodies and/or fragments and/or derivatives thereof are also suitable for isolation/purification using the methods described herein, as would be understood by those of ordinary skill of the art.

The proteins of interest isolated using the processes described herein may be formulated into compositions, some of which may be pharmaceutical compositions. Such compositions described herein may take any form suitable for use in research and/or administration to a host (e.g., a mammal such as a human being). Suitable forms include, for example, liquids, capsules, emulsions, granules, films, implants, liquid solutions, lozenges, multi-particulates, sachets, solids, tablets, troches, pellets, powders, and/or suspensions. Liquid formulations may include diluents, such as water and alcohols, for example, ethanol, benzyl alcohol, and the polyethylene alcohols, either with or without the addition of a pharmaceutically acceptable surfactant. Capsule forms may formed of gelatin (e.g., hard- or soft-shelled). Any of such compositions may include, for example, surfactants, lubricants, and inert fillers, such as lactose, sucrose, calcium phosphate, corn starch, and/or the like. Tablet forms may include, for example, excipients and/or other agents such as lactose, sucrose, mannitol, corn starch, potato starch, alginic acid, microcrystalline cellulose, acacia, gelatin, guar gum, colloidal silicon dioxide, disintegrants (e.g., croscarmellose sodium), talc, magnesium stearate, calcium stearate, zinc stearate, stearic acid, colorants, diluents, buffering agents, disintegrating agents, moistening agents, preservatives, and/or flavoring agents. Lozenges forms may also be used, typically with an inert base, such as gelatin and glycerin, or sucrose and acacia, emulsions, gels, and the like. The compositions may also prepared in lyophilized form. Other forms may also be suitable, as would be understood by one of skill in the art.

Pharmaceutical compositions may take any of the forms described above, or as may be known in the art. Pharmaceutical compositions may be prepared using one or more pharmaceutically acceptable carriers prior to use in research and/or administration to a host (e.g., an animal such as a human being). A pharmaceutically acceptable carrier is a material that is not biologically or otherwise undesirable, e.g., the material may be used in research and/or administered to a subject, without causing any undesirable biological effects or interacting in a deleterious manner with any of the other components of the pharmaceutical composition in which it is contained and/or reaction in which the same is used. The carrier would naturally be selected to minimize any degradation of the active agent and to minimize any adverse side effects in the subject, as would be well known to one of skill in the art. Suitable pharmaceutical carriers and their formulations are described in, for example, *Remington's: The Science and Practice of Pharmacy, 21$^{st}$ Edition*, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semi-permeable matrices of solid hydrophobic polymers containing polypeptides or fragments thereof. Matrices may be in the form of shaped articles, e.g., films, liposomes or microparticles. It will be apparent to those of skill in the art that certain carriers may be more preferable depending upon, for instance, the route of administration and concentration of composition being administered. Also provided are methods for treating disease by administering the composition (e.g., as a pharmaceutical composition) to a host in need of treatment. Suitable routes of administration include, for example, oral, buccal, rectal, transmucosal, topical, transdermal, intradermal, intestinal, and/or parenteral routes. Other routes of administration and/or forms of the compositions described herein may also be suitable as would be understood by those of skill in the art.

The compositions described herein may be used to treat various diseases, including but not limited to cancer and non-cancer conditions. Cancer- and/or cell growth-related conditions that may be treated include, for example, benign tumors, malignant tumors, warts, polyps, and the like. Examples of cancers that may be treated using the compositions described herein may include, but are not limited to bladder cancer, breast cancer, cervical carcinoma, colorectal cancer, esophageal cancer, lymphoma (e.g., Burkitt's, non-Hodgkin's), endometrial carcinoma, head and neck cancer, leukemia, liver cancer, lung cancer, nonpolyposis, melanoma, ovarian cancer, prostate cancer, and the like. Other cancer- and/or cell growth-associated diseases may also be treated as would be understood by one of skill in the art.

Typical diseases other than cancer that may be treated with the compositions described herein may include, for example, gastrointestinal disorders such as chronic diarrhea, diseases of the small intestine (e.g., enteritis including but not limited to duodenitis, jejunitis, ileitis), peptic/duodenal ulcer (e.g., Curling's ulcer), and malabsorption (e.g., coeliac's disease, tropical sprue, blind loop syndrome, Whipple's, short bowel syndrome, steatorrhea, Milroy disease)), diseases of the large intestine (e.g., appendicitis, colitis (e.g., pseudomembranous, ulcerative, ischemic, microscopic, collagenous, lymphocytic), functional colonic disease (IBS, intestinal pseudoobstruction/Ogilvie syndrome), megacolon/toxic megacolon, diverticulitis/diverticulosis), enterocolitis (e.g., necrotizing), inflammatory bowel disease ("IBD"), Crohn's disease, diarrehea (e.g., infectious, chronic), abdominal angina, mesenteric ischemia, angiodysplasia, proctitis (e.g., radiation proctitis), proctalgia fugax, anal fissure/anal fistula, anal abscess, arthritis, and the like. Other non-cancerous or cell-growth related diseases may also be treated as would be understood by one of skill in the art.

The proteins produced as described herein, and/or compositions comprising the same, may be used in research to detect proteins and/or nucleic acid function/expression in cells, tissues, and the like in vivo and/or in vitro. For example, the monoclonal antibodies may be used to stain cells to identify those expressing a particular protein. The monoclonal antibodies may also be conjugated to a detectable label and/or cytotoxic moiety. Other uses for the monoclonal antibodies produced as described herein are also contemplated as would be readily ascertainable by one of ordinary skill in the art.

Kits comprising the reagents required to isolate proteins from a cell-free supernatant are also provided. An exemplary kit may contain one or more solutions and/or buffers required for carrying out the methods (e.g., stock solution of calcium chloride, caprylic acid and/or PEG). The kit may also include various types of equipment (e.g., the apparatus illustrated in FIG. 18) that may be necessary or useful for carrying out the methods described herein. The kit may also include positive and/or negative controls that may be used to confirm the method is functioning as desired. Instructions for use may also be included. Kits comprising the proteins of interest and/or compositions comprising the same are also provided. In some embodiments, the kits comprise one or more containers comprising a composition described herein, or mixtures thereof, and instructions for in vitro or in vivo use. For example, the kit may include a container comprising a composition described herein and instructions for introducing the same to a cell in vitro, such as by adding the composition to a cell culture in bulk or to single cells. Regarding in vivo use, a kit may include a container containing a composition of a protein of interest and instructions for administering the same to an animal (such as a human being) to prevent or treat a disease condition. Other embodiments of kits are also provided as would be understood by one of ordinary skill in the art.

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

It must be noted that, as used in the specification and the appended claims, the singular forms "a", "an", and "the" include plural referents unless the context clearly dictates otherwise. Thus, for example, reference to a fragment may include mixtures of fragments and reference to a pharmaceutical carrier or adjuvant may include mixtures of two or more such carriers or adjuvants. The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

All references cited herein are hereby incorporated in their entirety by reference into this disclosure. A better understanding of the present invention and of its many advantages will be had from the following examples, given by way of illustration.

EXAMPLES

Example 1

Antibody Precipitation Using Polyethylene Glycol

A. Kinetics of Antibody Precipitation from Cell Culture Supernatant Using Polyethylene Glycol PEG precipitation kinetics were measured separately using the supernatants of hybridomas A, B07, B03, and C as starting material and one of PEG2000 (12.5%), PEG4000 (10.0%), PEG6000 (7.5%), PEG20000 (2.5%); pH values of 5.0, 7.0, or 8.5; and reaction times of 15, 30, 60, and 180 min were chosen. After 60 min, equilibrium of the precipitation process was reached indicated by leveling yield. For each antibody a different yield, depending on the parameters PEG size/concentration and pH value was observed. Yield of C precipitation was lower than for the other three antibodies, which may be explained by the higher solubility of C. However, the antibodies have similar precipitation kinetics. Antibody A precipitated with PEG4000 (10.0%), and exhibited the highest IgG yield. Hence, the precipitation of A with PEG4000 (10.0%) was used for the large scale tests.

The kinetic tests of A with PEG4000 (10.0%) in small and large scale (1.5 ml and 150 ml, respectively) showed that the concentration of the precipitated IgG in large scale was slightly higher. However, the kinetics of the small and large scale reactions were similar. Optimal precipitation time for the large scale reaction was determined to be 60 min.

B. PEG Concentration Screening

Various concentrations of PEG (0%, 1%, 2.5%, 5%, 7.5%, 10%, 12.5%, and 14%) were tested as precipitants for antibodies in culture supernatant of hybridomas B03 and B07. Antibody precipitation was effected at lower PEG concentrations with PEG of higher molecular mass. For instance, approximately 10% IgG is precipitated using PEG2000 at a concentration of 12.5% while PEG20000 precipitates the same amount at 5%. Precipitation reached about 80% using PEG4000, PEG6000 and PEG20000. This is explained by the liquid film remains at the wall of wells of the microtiter plates after removing the suspension with containing the precipitated protein. The residual 20% IgG is entrapped in this film. The pH of the starting solution did not influence precipitation yield in these experiments. Precipitation with lower PEG concentration showed little influence of pH. With increasing PEG concentration, the purity of the precipitated protein increased although a maximal yield is obtained at a certain PEG concentration which cannot be further increased (e.g., purity may decrease with increasing PEG concentration above a certain level). Purity of B03 is about 5 to 10% higher than purity of C which may relate to the composition of the different supernatants.

PEG precipitation screening in microtiter plates and experiments in 15 mL scale were used to determine the optimal precipitation parameters (14% PEG6000) for the various antibodies tested (B03, B07, A and C). The PEG concentration depends on the antibody concentration of the cell culture supernatant. If antibody concentration in the supernatant is higher, a lower PEG concentration is required and vice-versa with lower antibody concentration. PEG6000 was selected because a lower PEG concentration is needed compared to the lower molecular mass of PEG, while PEG20000 was not an option due to the high viscosity at concentrations above 20%.

C. pH Optimization

The pH-optimum for PEG precipitation (14% PEG6000) was determined for B03, B07, A and C. Irrespective of pH, a yield between 90 to 95% was obtained. Purity was not influenced by pH. The yield distinctions were observed because each antibody preparation had a different starting purity. PEG precipitation provided a purity increase of 20 to 40%.

D. Temperature Optimization

The influence of temperature on yield and purity of the mAb precipitation was also studied. The supernatants (B03, B07 and A) were precipitated at a 15 mL scale with 14% (v/v) PEG6000 at approximately pH 7.0. No significant influence of temperature on yield and purity was observed for any of the supernatants tested. The mAbs B03 and B07 exhibited slightly higher purity but also slightly lower yield at higher temperature (35° C.). At low temperatures (5° C.), the inverse was observed (a slightly higher yield but lower purity). For A, no influence of temperature was observed. Therefore, considering the trade-off between yield and purity and an easy adaptability of the process at large scale, room temperature (~25° C.) was selected for all further precipitations. In these studies, washing of the precipitate with 14% (v/v) PEG6000 at pH 7.0 was also evaluated. The analysis of the washed precipitate showed higher purity but lower yield in comparison with the non-washed precipitates.

E. PEG Precipitation Solubility Curves of Purified mAbs and Total Protein Impurities The solubility curves of the purified mAbs (B03, B07 and A) were also prepared. For calculation of the behaviour of a protein component in solution, with increasing concentration of PEG, the theory of Juckes (Juckes 1971a) expressed in the following equation was used:

$$\log S = \log S_0 - \beta \omega$$
$$\beta = \frac{\bar{v}}{2.303}\left(\frac{r_s + r_r}{r_r}\right)^3$$

In this equation S is the solubility, $S_0$ a constant, $\omega$ the polymer concentration, $\bar{v}$ the partial specific volume, $r_r$ the radius of the molecule excluded and $r_s$ is the cross sectional radius of the polymer. As B03 and B07 refer to the same antibody though different fermentations the solubility curves of B03 and B07 should be identical. Although the fit of the solubility curves of B03 and B07 exhibit different slopes (B03: −0.3767; B07: −0.3331) and intercepts (B03: 2.4643; B07: 1.9713), the confidence intervals (95%) are overlapping suggesting that there is a similarity between the curves. The intercept of the solubility curve provides the solubility of the mAb when no precipitant is present. For B07 and B03, the solubility was determined to be between 80 and 500 mg/mL. For A, a lower S0 between 3.2 and 32 mg/mL was determined. The solubility of a protein is dependent on the partial specific volume, the radius of the molecule and the properties of the precipitant (Arakawa and Timasheff 1985). The slope of solubility curve correlates with the hydrodynamic interaction of mAb and PEG and has an impact on PEG precipitation concentration (Juckes 1971a). Due to the PEG precipitation mechanism (volume exclusion effects (Arakawa and Timasheff 1985; Lee and Lee 1981; Lee and Lee 1979)), yield is not only dependent on the amount of PEG added but also on the concentration of mAb in the supernatant. For instance, when precipitating a mAb B07 using 14% (v/v) PEG6000, only 1.8 μg/mL of the mAb remains in the soluble fraction. Therefore, for a supernatant with a concentration of 1 mg/ml, a yield of 99.8% is theoretically possible. If the supernatant had a concentration of 10 mg/mL, precipitation would start at around 3% (v/v) PEG6000 and at around 9% (v/v) PEG6000 a theoretical yield of 99.9% could be achieved.

The solubility curves of purified mAb B07 and B03 as well as the solubility curves of the total protein impurities found in the flow-through of the protein A purified cell culture supernatant were also compared and found to be comparable. The protein impurities of the supernatants exhibit different solubilities (e.g., due to the difference in the fermentation strategies used). The flatness of the slopes indicates that the PEG has almost no influence on the solubility of the protein impurities (e.g., unlike the mAb solubility where the slopes are significantly steeper). Solubility at 0% (v/v) PEG6000 is, on the other hand, lower for the impurities than for the mAbs. Findings of these measurements are reason for the implementation of other novel continuous precipitation techniques (caprylic acid precipitation). The novel purification step has to separate the impurity fraction which also was precipitated with the mAbs during PEG precipitation.

F. PEG Precipitation Solubility Curves of Purified mAbs at Different pH Values

The solubility curves of B03, B07 and A were measured at pH values from 5.0 to 9.0 (for A from pH 4.5 to 9.0). It was determined that the precipitation with 14% PEG6000 value results in a log S of −2 (0.01 mg/mL not precipitated). These in findings are independent from pH. Sole exceptions are the pH values in the lower range. For B03 and B07, this pH 5.0 and 5.5 and for A are this pH 4.5, 5.0, 5.5 and 9.0. Reason for the difference of mAbs is the different pI values. However, increase of PEG concentration causes a decrease of log S and consequently an increase of yield. That mean mAb precipitations can be performed in an extremely wide pH range and only an increase of PEG concentration (up to 25%) is needed.

G. PEG Precipitations from CHO Cell Supernatants

Automated well plates screening of PEG precipitations were performed with five CHO cell culture supernatants, different PEG sizes (2000-20,000), concentrations (0-14%), and different pH values (5.0-8.5). Yield and purity were determined with analytical protein A CIM disks (BIA) and showed an optimum with 14% PEG6000 at pH 7.0. The data is presented in FIG. 1.

Example 2

Combined CaCl$_2$/PEG Precipitation

The precipitation mechanism with polyethylene glycol (PEG) precipitation is a volume exclusion reaction. PEG binds the water molecules, so that the hydrate layer around the protein will be drained and proteins agglomerate. PEG can be used to precipitate large proteins (e.g., mAbs as shown above) as well as DNA. For separation of DNA, CaCl$_2$ co-precipitation may be performed. CaCl$_2$ with PO$_4^{3-}$ causes a formation of different kinds of insoluble calcium phosphate precipitates which co-precipitate large and negatively charged molecules. The parameters of a CaCl$_2$/PEG co-precipitation study are shown in Table 1.

TABLE 1

|  | Antibodies | | | | |
|---|---|---|---|---|---|
| Yield and purity parameters | mAb1 | mAb2 | mAb3 | mAb4 | mAb5 |
| Antibody yield | | | | | |
| Yield after affinity chromatography [%] | 83 | 100 | 75 | 79 | 96 |
| Yield after CaCl$_2$/PEG precipitation [%] | 81 | 78 | 96 | 90 | 94 |

TABLE 1-continued

| Yield and purity parameters | Antibodies | | | | |
|---|---|---|---|---|---|
| | mAb1 | mAb2 | mAb3 | mAb4 | mAb5 |
| High molecular weight impurities (HMWI)/aggregates | | | | | |
| HMWI cell free harvest [%] | 1.34 | 3.82 | 18.28 | 5.03 | 1.90 |
| HMWI after affinity chromatography [%] | 0.50 | 0.60 | 5.10 | 0.80 | 0.70 |
| HMWI after CaCl$_2$/PEG precipitation [%] | 0.40 | 0.50 | 11.50 | 2.30 | 2.30 |
| HMWI comparison (harvest/affinity) [fold] | 2.7 | 6.4 | 3.6 | 6.3 | 2.7 |
| HMWI comparison (harvest/prec) [fold] | 3.4 | 7.6 | 1.6 | 2.2 | 0.8 |
| Host cell proteins (HCP) | | | | | |
| Cell free harvest HCP [ppm] | 255,637 | 388,296 | 160,115 | 676,304 | 275,377 |
| Affinity chromatography HCP [ppm] | 8,170 | 5,645 | 1,440 | 5,000 | 299 |
| CaCl$_2$/PEG precipitation [ppm] | — | 35,929 | 46,072 | 53,312 | 73,700 |
| HCP comparison (harvest/affinity) [fold] | 31.3 | 68.8 | 111.2 | 135.3 | 921.0 |
| HCP comparison (harvest/prec) [fold] | — | 10.8 | 3.5 | 12.7 | 3.7 |

Figure 2:
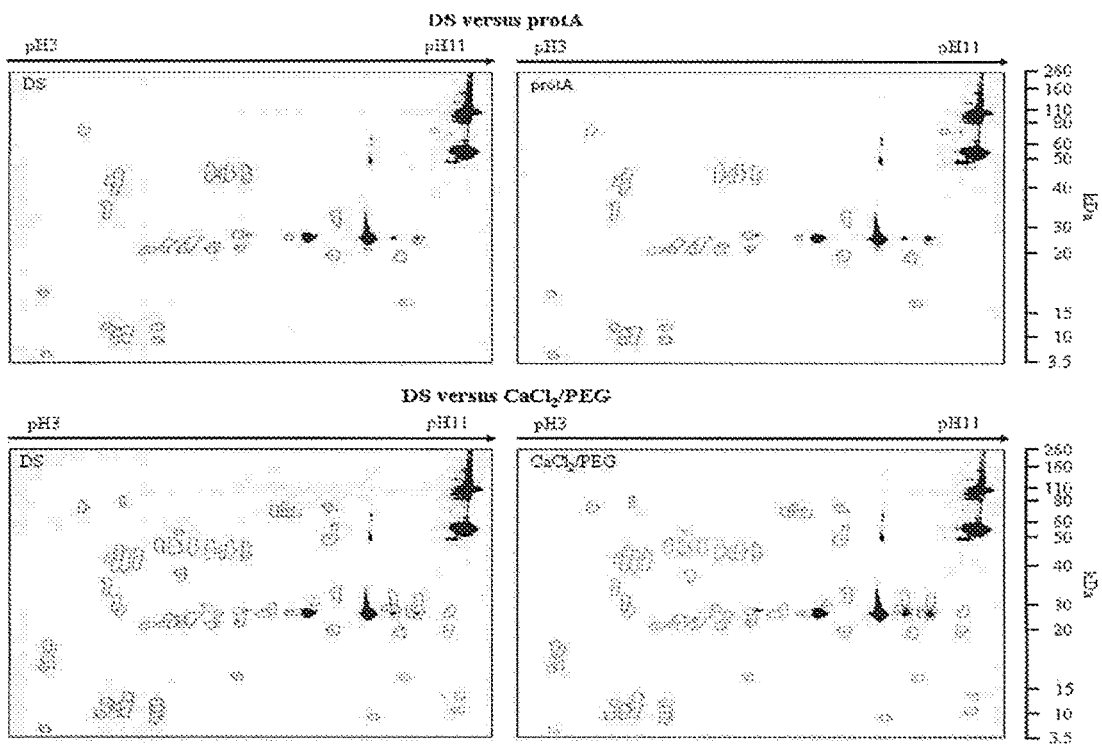
FIG. 2. 2-D gel electrophoresis results.

As shown therein, the yield of this co-precipitation was in the range of 85-90%; SEC showed a comparable HMWI and HCP reduction between protein A chromatography and CaCl$_2$/PEG purification; HCP ELISA of CaCl$_2$/PEG precipitation was between 3 and 13 fold reduction and has to be between 30 and 900 (protein A). Any inconsistencies in the purity analysis by SEC and HCP ELISA might be caused by interference of Ca$^{2+}$ in the HCP ELISA. Protein A (protA) and CaCl$_2$/PEG purification show equal decrease of spots on 2D DIGE compared to DS (FIG. 2 and Table 2). Protein A chromatographic purification was found to reduce more HCP than CaCl$_2$/PEG precipitation.

TABLE 2

| spot behavior | DS vs protA | | DS vs CaCl$_2$/PEG | |
|---|---|---|---|---|
| | spots | spots [%] | spots | spots [%] |
| decreased | 15 | 5.8% | 15 | 5.8% |
| similar | 208 | 80.6% | 160 | 62.0% |
| increased | 35 | 13.6% | 83 | 32.2% |

Example 3

Caprylic Acid (CA) Precipitation for Improved HCP Reduction

Figure 3:
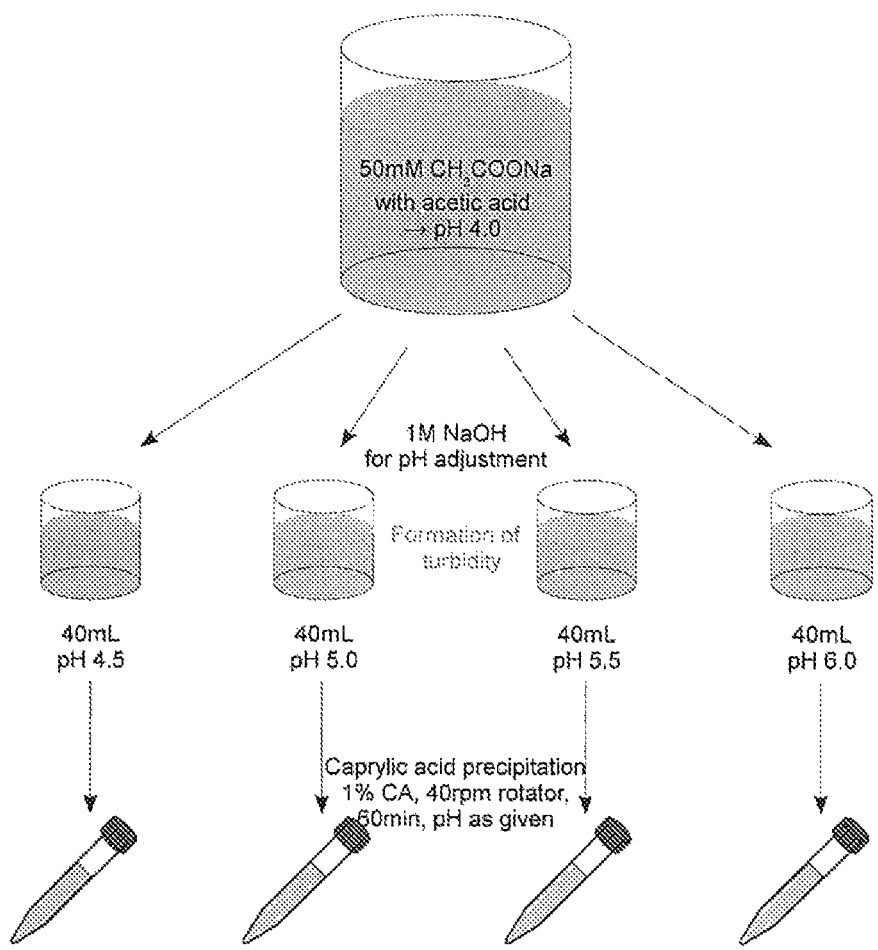
FIG. 3. Exemplary caprylic acid (CA) precipitation protocol.

A major improvement in CA precipitation was the stabilization of pH using sodium acetate. For reaching buffering capacity, the sodium acetate amount was calculated (approximately 50 mM) according to relevant literature (Mohanty and Elazhary 1989; Raweerith and Ratanabanangkoon 2003). Therefore, a concentrated buffer solution was mixed with CHO cell culture supernatant to have a concentration of 50 mM sodium acetate prior CA precipitation in solution (pH adjustment slightly increases CH$_3$COONa concentration). The buffered supernatant was adjusted with acetic acid to pH 4.0 and subsequently divided in four similar portions. Each portion was adjusted with sodium hydroxide to a certain pH (4.5, 5.0, 5.5, and 6.0). This was done for two mAbs (B03 and B07) and three times to examine different temperatures during process. The first process alignment was performed, centrifuged and stored at room temperature, the second was performed and centrifuged at room temperature and stored at 4° C. and the third was performed at room temperature and centrifuged and stored at 4° C. (FIG. 3).

Samples from pH/buffer tests were collected and measured by using SEC and Bradford assay. Comparison of the different tempered process alignments (different pH values (4.5, 5.0, 5.5 and 6.0)) showed no differences in yield. The CA precipitation results in a loss of 10 to 20% yield. After pH adjustment yield decreases about 20 to 30%. Due to this reason an improvement of pH adjustment is necessary. Highest yield was reached at lowest pH (pH 4.5). Reason could be the lower salt concentration at low pH or even the low pH. Hence for verifying this assumption an exact pH adjustment is needed to have lower salt concentrations. For yield determination, IgG areas of size exclusion chromatograms from cell culture supernatant and samples were compared. Reason for change of yield determination method is the sample pH which is around 4.5. This value is too near by the elution pH (pH 3) of the analytical affinity chromatography for getting reproducible data.

TABLE 3 mAb Yield After CA Precipitation at Different pH Values (mAb concentration by SEC)

| | Precipitation step | B03 | pH 4.5 | pH 5.0 | pH 5.5 | pH 6.0 | B07 | pH 4.5 | pH 5.0 | pH 5.5 | pH 6.0 |
|---|---|---|---|---|---|---|---|---|---|---|---|
| sample | pH [mg/mL] | 2.40 | 2.04 | 1.96 | 1.83 | 1.77 | 1.81 | 1.40 | 1.37 | 1.32 | 1.28 |
| | pH [%] | | 85% | 82% | 76% | 74% | | 77% | 75% | 73% | 71% |
| 1 | pH + CA [mg/mL] | | 1.86 | 1.71 | 1.46 | 1.53 | | 1.11 | 1.17 | 1.11 | 1.14 |
| | CA [%] | | 91% | 87% | 80% | 86% | | 79% | 86% | 84% | 89% |
| | pH + CA [%] | | 77% | 71% | 61% | 64% | | 68% | 65% | 62% | 63% |
| 2 | pH + CA [mg/mL] | | 1.82 | 1.65 | 1.52 | 1.60 | | 1.25 | 1.16 | 1.11 | 1.16 |
| | CA [%] | | 89% | 84% | 83% | 90% | | 89% | 85% | 84% | 90% |
| | pH + CA [%] | | 76% | 69% | 63% | 67% | | 69% | 64% | 61% | 64% |

TABLE 3-continued mAb Yield After CA Precipitation at Different pH Values (mAb concentration by SEC)

| | Precipitation step | B03 | pH 4.5 | pH 5.0 | pH 5.5 | pH 6.0 | B07 | pH 4.5 | pH 5.0 | pH 5.5 | pH 6.0 |
|---|---|---|---|---|---|---|---|---|---|---|---|
| 3 | pH + CA [mg/mL] | | 1.89 | 1.79 | 1.55 | 1.60 | | 1.26 | 1.19 | 1.12 | 1.10 |
| | CA [%] | | 92% | 91% | 85% | 90% | | 90% | 87% | 85% | 86% |
| | pH + CA [%] | | 79% | 73% | 64% | 67% | | 70% | 66% | 62% | 61% |

In Table 4, data of total protein measurements are listed. The process alignment comparison showed no significant difference in protein concentration. That implies temperature changes have no impact on the process. Clearly observable is the total protein decrease after pH adjustment with highest reduction at pH 4.5. Total protein reduction after CA precipitation was almost constant with total protein yield between 60 and 70%. The highest yield and total protein reduction occurs at pH 4.5. Samples with this pH were selected for future measurements.

TABLE 4

Total protein data after CA precipitation at different pH values (Bradford)

| | Precipitation step | B03 | pH 4.5 | pH 5.0 | pH 5.5 | pH 6.0 | B07 | pH 4.5 | pH 5.0 | pH 5.5 | pH 6.0 |
|---|---|---|---|---|---|---|---|---|---|---|---|
| sample | pH [mg/mL] | 1.81 | 1.29 | 1.45 | 1.47 | 1.52 | 1.34 | 0.81 | 0.83 | 0.80 | 0.89 |
| | pH [%] | | 71% | 80% | 81% | 84% | | 61% | 62% | 59% | 66% |
| 1 | pH + CA [mg/mL] | | 0.83 | 0.99 | 0.86 | 0.89 | | 0.55 | 0.57 | 0.50 | 0.52 |
| | CA [%] | | 64% | 68% | 59% | 59% | | 68% | 69% | 63% | 58% |
| | pH + CA [%] | | 46% | 55% | 48% | 49% | | 41% | 70% | 60% | 65% |
| 2 | pH + CA [mg/mL] | | 0.74 | 3.60 | 1.04 | 1.12 | | 2.03 | 0.92 | 0.67 | 0.57 |
| | CA [%] | | 57% | 248% | 71% | 74% | | 251% | 111% | 84% | 64% |
| | pH + CA [%] | | 42% | 198% | 57% | 62% | | 151% | 68% | 50% | 43% |
| 3 | pH + CA [mg/mL] | | 0.86 | 1.03 | 1.02 | 1.05 | | 0.54 | 0.56 | 0.57 | 0.62 |
| | CA [%] | | 67% | 71% | 69% | 69% | | 67% | 67% | 71% | 70% |
| | pH + CA [%] | | 48% | 57% | 56% | 58% | | 40% | 42% | 43% | 46% |

Comparison of size exclusion chromatograms of the samples of B03 and B07 with highest mAb yield and lowest total protein concentration (at pH 4.5) show a slight reduction of high and low molecular weight impurities after pH adjustment (FIG. 4A-B). This reduction increased after CA precipitation but major impurities were not removed.

The samples were also compared by HCP-ELISA. Table 5 the shows ELISA data after pH adjustment and CA precipitation. The host cell reduction (HCP) was around 2 fold after pH adjustment and after CA precipitation above 10 fold. The reduction of HCP with CA precipitation is similar to PEG precipitation (Jungbauer et al. 2011) with the exception that SEC chromatograms show an impurity reduction after PEG precipitation. Reason could be the separation of different proteins with the different methods. Hence a combination of PEG and CA precipitation has to be evaluated.

TABLE 5

HCP-ELISA data (Cygnus) of CA precipitation sample at pH 4.5

| mAb | SN [ng/mL] | pH change (pH 4.5) HCP [ng/mL] | CA precipitation | pH change (pH 4.5) Fold HCP reduction [ppm] | CA precipitation |
|---|---|---|---|---|---|
| B03 | 195476 | 78594 | 16659 | 2.5 | 12 |
| B07 | 59992 | 33459 | 5711 | 2 | 11 |

The DNA content of "pH 4.5 samples" of all mAbs (B03 and B07) was also determined (Table 6). The pH adjustment showed a reduction of DNA from 3 to 10 fold. After CA precipitation the DNA content was below limit of detection. This data are comparable with the SEC chromatograms. Upon CA precipitation a distinct reduction of high molecular weight impurities occurs.

TABLE 6

DNA data (Picogreen) of CA precipitation sample at pH 4.5

| mAb | SN [ng/mL] | pH change (pH 4.5) DNA [ng/mL] | CA precipitation | pH change (pH 4.5) Fold DNA reduction [ppm] | CA precipitation |
|---|---|---|---|---|---|
| B03 | 2470 | 236 | <q | 10.5 | <q |
| B07 | 954 | 302 | <q | 3 | <q |

Parameter Screening of CA Precipitation

For optimization of caprylic acid precipitation a screening of salt concentration, mixing speed and reaction time were performed. Caprylic acid concentration (1% CA) and pH value (pH 5.5) were kept constant. FIGS. 5A and 5B illustrate the influence of NaAc salt concentration on yield of B03 and B07. Higher salt concentration caused a decrease of yield. This could be du to a pH shift induced at higher salt concentration. As shown previously (Jungbauer et al. 2011), yield is decreased with decreasing pH. Comparison of FIGS. 5A and 5B points out the influence of pH adjustment prior CA precipitation (from app. pH 7 to 5.5). Yield data of the figures were set in relation to cell culture supernatant concentration (FIG. 5A) and in relation to pH adjusted cell culture supernatant (FIG. 5B). Comparison of yields showed differences around 10% for both mAbs (B03 and B07) at all salt concentrations.

The optimal mixing speed during CA precipitation was also investigated. Precipitation was performed at pH 5.5 for 60 minutes with 50 mM sodium acetate and 1% CA as precipitant. The mixing speed tests were accomplished with 5, 10, 20, 30 and 40 rpm on a rotator. This setup was realized with both mAbs (B03, B07) for samples compared with cell culture supernatant and pH-adjusted cell culture supernatant. As noted above, pH adjustment causes a significant reduction of yield (approximately 10%). Furthermore, the test of mixing speed showed that yield decreased with increasing precipitation time. Highest yield could be reached with a mixing speed of 5 rpm (noting that host cell protein (HCP) data was not collected). The loss of yield at higher mixing speeds could result from increased mechanical pressure on proteins which caused a protein phase transition from aqueous to organic phase (caprylic acid) and subsequently precipitation and denaturation as a consequence of the organic environment. Another reason could be a direct interaction of caprylic acid with negatively charged proteins/IgG. Ideal mixing speed may be between 5 or 10 and 30 rpm to provide a suitable reduction of HCP with low loss of yield.

Reaction time of CA precipitation was also studied. Precipitation from B03 and B07 culture supernatants (including pH-adjusted culture supernatant) was performed at pH 5.5 with 50 mM sodium acetate and 1% CA as precipitant at a constant mixing speed (40 rpm (rotator)) for 5, 15, 30, 45 and 60 minutes. As described above, pH adjustment resulted in loss of IgG (approximately 10%). Increased reaction time was found to decrease yield. The highest yield could be reached with a reaction time of 5 minutes (noting that host cell protein (HCP) data was not collected). The loss of yield at longer reaction times could relate to an increase of mechanical pressure on proteins which caused a protein phase transition from aqueous to organic phase (caprylic acid) followed by protein precipitation (also IgG) as a consequence of the organic environment or a direct interaction of caprylic acid with negatively charged proteins could be the reason for protein precipitation and denaturation. Ideal reaction time is most probably located between 15 and 45 minutes to provide a suitable reduction of HCP with low loss of yield.

Example 3

Combination of PEG and CA Precipitation for Improved HCP Reduction

Figure 6:
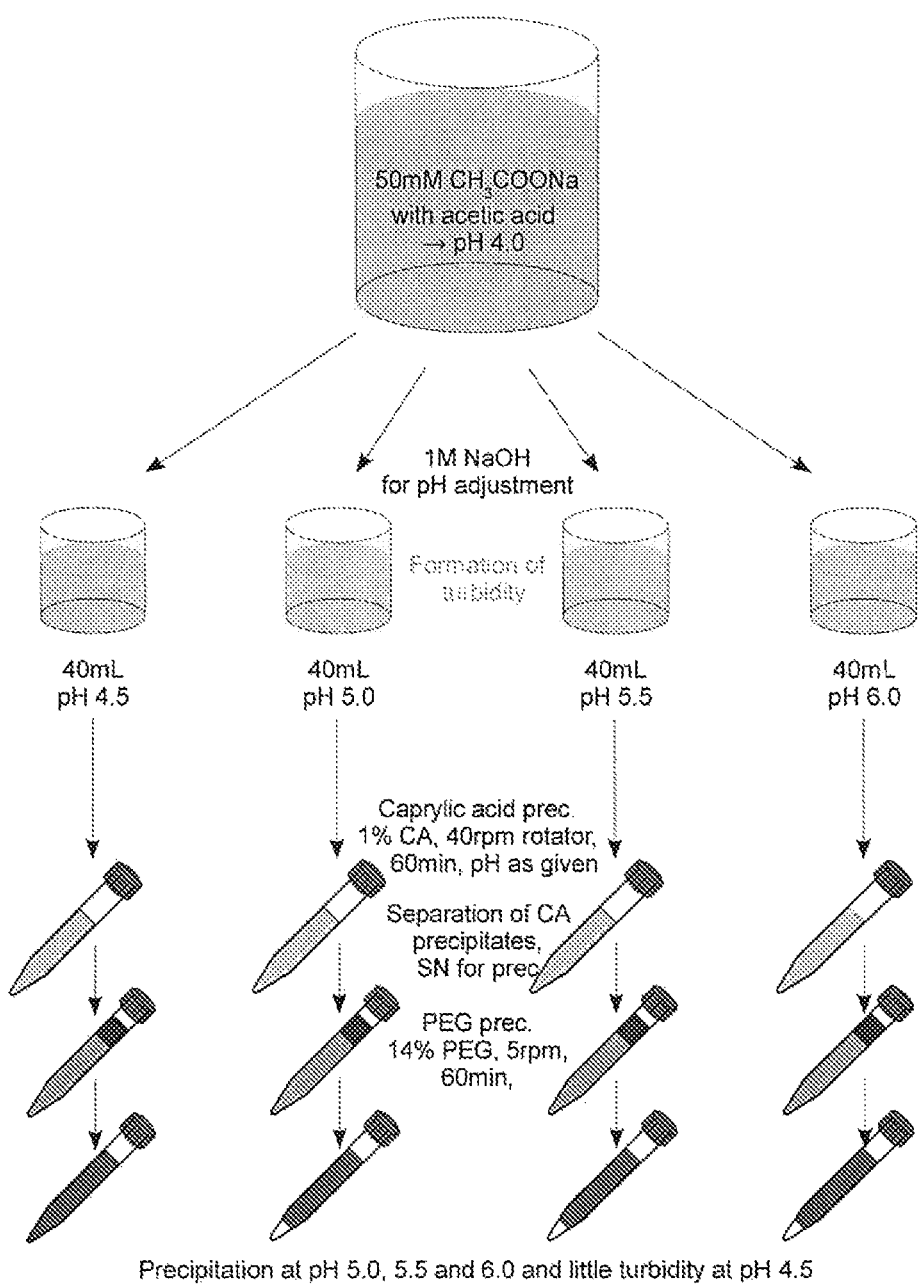
FIG. 6. Exemplary CA/PEG precipitation protocol.

The CA precipitation supernatants samples of the room temperature process alignment were than used for precipitation with 14% PEG6000 to get an estimation of the CA/PEG precipitation combination. Samples were treated like PEG precipitation described previously. The CA precipitation alignment followed by PEG precipitation is shown in FIG. 6. Yield of CA/PEG precipitated samples were measured with SEC (BIO-SEC3, Agilent). The purities were determined with HCP-ELISA. Data of both mAb (B03 and B07) are shown in FIGS. 7A and 7B. The combination of CA and PEG precipitation exhibited similar results for both mAbs. After CA precipitation, yield was between 60 and 80% and HCP reduction was around 10-fold for all pH values. The yield of the subsequent PEG precipitation dropped down to 40 to 50% for samples with a pH of 5.0 to 6.0. About a 10% yield was obtained at pH 4.5. After PEG precipitation at pH 5.0, HCP concentrations started with 200- to 400-fold HCP reduction and approximately 100 fold HCP reductions at pH 6.0. Thus, the greatest reduction of HCP was observed at pH 5.0. The highest yield for B03 was observed at pH 6.0 and for B07 between pH 5.0 and 6.0. However, the yield was only 40%. To improve yield, a higher PEG concentration could be selected or the pH adjusted higher prior to PEG precipitation.

For yield improvement of PEG precipitation, a screening of PEG concentration was performed. Samples of the CA precipitation supernatant (e.g., supernatant after caprylic acid precipitation) were precipitated with three different PEG concentrations (14, 18 and 21%). The precipitations were performed with both mAbs (B03 and B07), with process step alignments 1 and 3 (at room temperature and 4° C.) and for pH values 4.5, 5.0, 5.5 and 6.0. An increase in yield was observed for both mAbs by similar precipitation parameters. Comparison of the different process steps alignments showed that temperature has no impact on yield. An increased PEG concentration resulted in higher yield compared to the starting value after CA precipitation. Also higher pH values cause an increased yield. Comparison of PEG precipitation data and these pH values show an increase of pH with increasing PEG concentration and hence an increase of yield. Hence, raising pH to approximately pH 7.0 after CA precipitation and an increase of PEG concentration is expected to improve yield. Novel results are antithetical to past experience of PEG precipitation where an increase in PEG concentration overrules pH effects. The low yield with increased PEG concentration at low pH could be lead back to CA presence.

The bar charts shown in FIGS. 8A and 8B are labelled with the pH measured for the SN after PEG precipitation. For PEG precipitation, pH values start with the lower pH for precipitation with 14% PEG and ends up with the higher pH for precipitation with 21% PEG. The pH for precipitation with 18% PEG is in between the highest and the lowest pH value.

Previous screenings of the optimal pH (4.5 to 6.0) was performed and showed a high host cell protein (HCP) reduction but low yield after PEG precipitation. The CA precipitation was also performed at three pH values (4.5, 5.0 and 5.5) to separate HMWI and HCP precipitates, which was followed by adjustment of the pH to about 7 (between 6.9 and 7.1). In comparison to the previous data, the pH change resulted in an increased yield after PEG precipitation (14% PEG6000). However, a slight increase in HCP amount was also observed. All pH value tests were performed with two mAbs (B03 and B07); data is presented in FIGS. 9A and 9B. As shown therein, the highest yield after CA precipitation was reached at pH 4.5. The highest HCP reduction and overall yield was at pH 5.0 for mAb B03 and pH 4.5 for B07. Due to this data a screening of initial buffer concentration for further improvement of yield after CA precipitation and an enhancement of PEG concentration to increase yield after CA/PEG precipitation are required.

For further improvements of CA/PEG precipitation, a sodium acetate buffer screening was performed. CA precipitation was accomplished with 1% CA at 40 rpm for 60 minutes (Rotator) at pH 5.5. Only the sodium acetate buffer concentration was varied (5, 10, 20, 40, 50, 100, 125 and 200 mM sodium acetate). Prior to PEG precipitation, the CA phase and precipitates were separated from supernatant.

Subsequently, the pH value of the supernatant was adjusted to approximately pH 7 and PEG6000 was added to a final concentration of 14% (v/v). FIGS. 10A and 10B show the yield and HCP reduction data for B03 and B07, respectively, after CA and CA/PEG precipitation at different salt concentrations. Highest yield and HCP reduction was achieved at low salt concentration (5 mM sodium acetate). Thus, the pH is affected by the salt concentration and itself affects yield. A further increase of yield after PEG precipitation could be achieved with increased PEG concentration. However, a change of the buffer system from sodium acetate to sodium citrate (buffers in the same range) may also improve yield and purity of mAb. A similar buffer and salt concentration screening with sodium citrate was therefore performed.

The sodium citrate pH screening of B03 (FIG. 11A) and B07 (FIG. 11B) was performed with the same parameter as at sodium acetate pH screening. The only difference from the previous studies was the exchange of sodium acetate with sodium citrate. Comparisons of citrate buffer data and with acetate buffer data show increased yield and purity after PEG precipitation with sodium acetate buffer. Influence of the pH values was similar for both buffer systems (pH 4.5 precipitation optimum).

The sodium citrate salt concentration screening (FIGS. 12A and 12B) was performed in the same manner as the sodium acetate salt concentration screening. Data showed reduced yield after CA but increased yield and purity after PEG precipitation. Especially at higher salt concentrations (100 to 200 mM) such values occurs. Reason for that might lead back to salt-protein or salt-precipitant interaction. These findings stand in contrast to the sodium acetate data where the highest yield was achieved at low salt concentration and which induces low pH and as consequence higher yield.

Given these results, an improved series of tests using B03 and B07 cell culture supernatants with 100 and 200 mM sodium citrate as the buffer system and three different PEG concentrations (14%, 18% and 21% [v/v]) for mAb precipitation was performed. Parameters such as mixing speed (40 rpm), mixing time (60 min), and reaction temperature were applied as in the previous screenings. The pH was adjusted to pH 4.5 prior CA precipitation and to approximately 7 (pH 6.90 to 7.10) prior to PEG precipitations. The data for B03 is presented in FIG. 13A. At 100 mM sodium citrate, the total yield was observed to increase with increasing PEG concentration but the purity to decrease. At 200 mM sodium citrate, both yield and purity decreased with increased PEG concentration. This antithetic manner could be induced by the change of salt-protein or salt-precipitant interactions at changing salt concentrations. For B03, the highest total yield as well as HCP reduction was achieved using 100 mM sodium citrate and 21% PEG. The data for B07 is presented in FIG. 13B. At 100 mM sodium citrate, no significant change in yield and purity with increasing PEG concentration. At 200 mM sodium citrate, increased PEG concentration did not appear to increase yield; a decrease in purity with higher PEG concentration was, however, observed. The highest yield for B07 was determined to result from 100 mM sodium citrate and 21% PEG, but highest HCP reduction was reached with 200 mM HCP and 14% PEG. Comparison of this data showed an inferior yield and purity of B07 which could result from the lower mAb concentration in cell culture supernatant (B03=2.6 mg/mL; B07=1 mg/mL). Based on these findings, the parameters 100 mM sodium citrate and 21% PEG were selected for further screenings.

For further purity improvement a CA concentration screening for CA/PEG precipitation was done. Therefore the parameters mixing speed, mixing time, buffer system, salt concentration, pH adjustment and PEG concentration were assumed from former screening findings (40 rpm on rotator; 60 min reaction time; 100 mM sodium citrate; pH adjusted with sodium hydroxide and/or citric acid; prior CA precipitation 4.5, prior PEG precipitation 6.9 to 7.1). The CA concentrations were range from 0.5 to 10% (0.5, 1.0, 2.0, 4.0, 6.0, 8.0 and 10.0%). FIGS. 14A and 14B show yield and purity of the CA concentration screening for both mAbs. Comparisons of all yield data shows no influence of CA concentration. An exception was the total yield data for the B07 sample at 1% CA which was two times higher than the others, most likely due to the starting concentration of cell culture supernatant (which was concentrated with protein A purified mAb up to 2.5 mg/mL (original concentration of B07=1 mg/mL)). The purity data of both mAb indicated no significant impact of the CA concentration. Precipitation of B03 with 10% CA showed a higher HCP reduction which is negligible (or outlier analysis) because of the difficult manageability of such high CA concentrations. Yield data of FIGS. 14A and 14B were determined with SEC, due to the original problem relating to sample measurement at low pH. As this problem was solved as described above, yield measurements may be performed by analytical affinity chromatography (FIGS. 15A and 15B). Comparison of these data show similar purity values. The measured yield data (analytical affinity chromatography, protein A), however, were approximately 20% higher. These finding lead to the assumption, that all prior measured yield values (with SEC) may be too low (Jungbauer et al. 2010a).

Samples from the CA concentration screening study (1% CA for precipitation from FIGS. 16A and 16B) were analyzed for yield and purity. Concentration of mAb was for both cell culture supernatants at around 2.5 mg/mL (B03=2.65 mg/mL and B07=2.59 mg/mL). The yield and purity data is presented in Tables 7 and 8.

TABLE 7

Yield (protein A affinity chromatography) and purity data from CA/PEG precipitation of B03 measured by SEC TSK3000 SWXL, Tosho, 280 nm (BOKU)) and SEC TSK3000 SWXL, Tosho, 210 nm (Nov))

| B03 | PEG (BOKU) (%) | PEG (Nov) (%) |
|---|---|---|
| Monomer purity (%) | 97.9 | 96.7 |
| Aggregate (%) | 2.1 | 3.3 |
| Yield (%) | 81 | 81 |
| HCP (ppm) | 3711 | 4404 |
| HCP reduction (x, -fold) | 72 | 65 |

TABLE 8

Yield (protein A affinity chromatography) and purity data from CA/PEG precipitation of B07 measured by SEC TSK3000 SWXL, Tosho, 280 nm (BOKU)) and SEC TSK3000 SWXL, Tosho, 210 nm (Nov))

| B07 | PEG (BOKU) (%) | PEG (Nov) (%) |
|---|---|---|
| Monomer purity (%) | 98.9 | 95.5 |
| Aggregate (%) | 1.1 | 4.5 |
| Yield (%) | 84 | 84 |
| HCP (ppm) | 3038 | 1019 |
| HCP reduction (x, -fold) | 102 | 107 |

These comparisons showed that all measured parameter are comparable, although the content of aggregates (high molecular weight impurities=HMWI) were measured to be higher using the Nov system. This may be due to the different wavelength used for the determination (280 nm vs. 210 nm) or for other reasons. The recovery of mAb was above 80% and the reduction of HCPs (host cell proteins) was about 100-fold. However, size exclusion chromatogram comparison of cell culture supernatant and CA/PEG purified mAb are for both mAbs shown in FIGS. 16A and 16B. A significant reduction of HMWI (aggregates) and LMWI (low molecular weight impurities) resulting from these processes is apparent therein.

CA/PEG precipitation screening for optimal salt kind (acetate or citrate), concentration (5-200 mM) and pH values (4.5, 5.0, 5.5) with yield and HCP determination after precipitation steps led to the selection of 100 mM sodium citrate, pH 4.5 as the precipitation optimum. FIGS. 17A-F and Table 9 present yield, SEC, HCP and HMWI data for the optimized CA/PEG precipitation for two exemplary monoclonal antibodies.

TABLE 9

| mAb1 | PEG/CA | Protein A chromatography | mAb2 | PEG/CA | Protein A chromatography |
|---|---|---|---|---|---|
| Monomers [SEC] (%) | 97.9 | 99.0 | Monomers [SEC] (%) | 98.9 | 99.3 |
| HWMI [SEC] (%) | 2.1 | 0.5 | HWMI [SEC] (%) | 1.1 | 0.6 |
| Yield [ALC] (%) | 81.0 | 83.3 | Yield [ALC] (%) | 84.0 | 99.9 |
| HCP [ELISA] (ppm) | 3711 | 8170 | HCP [ELISA] (ppm) | 3038 | 5645 |
| HCP reduction (fold) | 72 | 40 | HCP reduction (fold) | 102 | 62 |

SUMMARY

Two precipitation combinations were developed CaCl$_2$/PEG and CA/PEG. CaCl$_2$ precipitation serves for separation of HMWI such as dsDNA and aggregates. CA precipitation was used for HMWI as well as HCP reduction and PEG precipitation separates mAbs from LMWI. CaCl$_2$/PEG precipitation tests were performed with five different CHO cell culture supernatants and showed data that were roughly comparable to protein A chromatographic purification. CA/PEG precipitation lead to yield between 80 and 85% with approx. 3000 ppm HCP and HMWI below 2%. This precipitation is highly competitive to protein A chromatography.

Example 5

Caprylic acid precipitation, PEG precipitation and CaCl$_2$ precipitation may also be combined into a single process. In an exemplary embodiment, a clarified cell culture supernatant was first precipitated using 100 mM sodium citrate (NaCit), pH 4.5, 1% caprylic acid and the resulting precipitate removed to provide a secondary supernatant. Antibody was then be precipitated from the secondary supernatant using 21% PEG at pH 7 and isolated and resuspended in an appropriate buffer. This preparation was then be treated using calcium chloride (250 mM CaCl$_2$, pH 8.5) to precipitate further impurities (e.g., DNA). The precipitated precipitated impurities were then removed to provide a solution comprising antibodies. This solution was then resuspended in an appropriate buffer and the antibodies therein precipitated (e.g., washed) in 25% (v/v) ethanol, pH 6.5, −10° C. The results of this process (FIGS. 18A and B) are summarized in Table 10:

TABLE 10

| Yield (%) | HCP (ppm) | HCP (fold) | HMWI (%) | dsDNA (ng/mL) |
|---|---|---|---|---|
| 100 | 97.608 | 0 | 2,931 | 6.374 |
| 93 | 27.357 | 4 | 2,134 | 1.363 |
| 86 | 12.158 | 8 | 1,343 | 258 |
| 77 | 1968 | 29 | 0.000 | #NV |
| 69 | 277 | 253 | 0.000 | 94 |

In some embodiments, ultrafiltration, diafiltration and/or ion exchange chromatography may be added as an additional step to further purify the antibody.

Example 6

Continuous Production of mAbs

Figure 19:
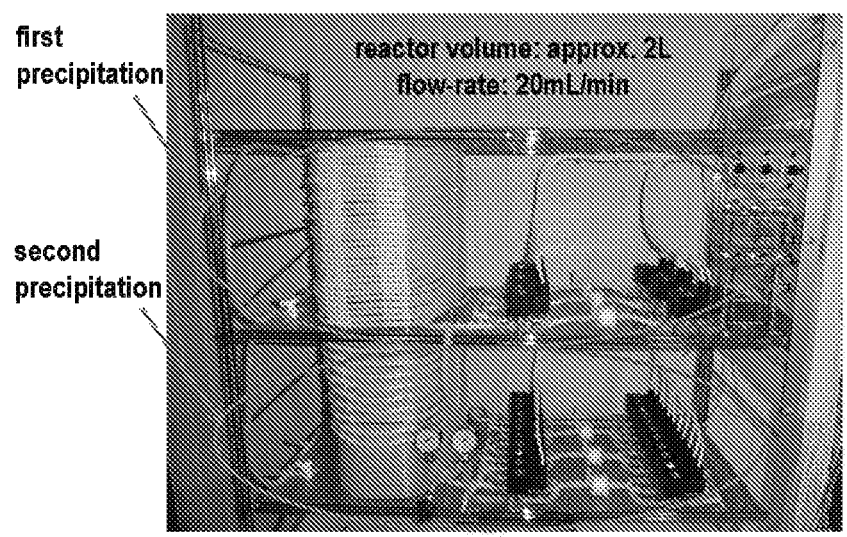
FIG. 19. Exemplary reactor for mAb purification.

As described above, precipitation methods such as calcium chloride (CaCl$_2$), polyethylene glycol (PEG), and caprylic acid (CA) precipitation were screened and combined for reaching at least equal yield and purity as for conventional first capture steps. The final process was a combination of two precipitation methods which is competitive to protein A affinity chromatography and may be driven continuously in a tubular reactor. After development of this precipitation process, a lab scale pilot plant was designed and constructed (FIG. 19). This pilot plant consists of a two-step precipitation reactor with an approximate two liter volume and a flow rate of 20 ml/min; 20 m silicon tubes (5 mm diameter) for precipitation area; magnetic valves and filter units with a black flush mode for precipitate separation; wherein an analogous system control with the possibility to switch the filter state by hand and/or both precipitation lines can be run independently. However, for replacement of the whole mAb downstream processing, further purification/polishing steps have to be implemented. Therefore an additional precipitation method (cold ethanol precipitation, CEP) was tested and several combinations of all methods were performed. Eventually, two out of twelve different precipitation alignments showed remarkable good yield (approx. 70%) and purity (approx. 280 ppm HCP and no aggregates) data. Both processes are column-free and consist of only four purification steps (instead of seven or eight) which can be operated continuously. This novel precipitation process may be driven continuously to replace at least the first capture step (protein A affinity chromatography) but most likely the whole of state of the art mAb purifications process.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method for isolating a protein of interest from nucleic acids and other host cell proteins present in cell culture supernatant comprising said protein, the method comprising:
   (a) combining said cell culture supernatant with a first precipitating agent to remove precipitated proteins and/or other components to produce a secondary cell culture supernatant, the first precipitating agent being calcium chloride and/or a fatty acid;

(b) introducing a precipitating polymer into said secondary cell culture supernatant to precipitate the protein of interest from the secondary cell culture supernatant.

2. The method of claim 1, wherein the precipitating polymer is polyethylene glycol (PEG).

3. The method of claim 2, wherein the PEG is selected from PEG2000, PEG4000, PEG6000 and PEG20000.

4. The method of claim 2, wherein the PEG is introduced into the secondary cell culture supernatant in an amount of from about 5 to about 30%.

5. The method of claim 1, wherein the pH in step (b) is about from 4 to 9.

6. The method of claim 5, wherein the pH is from 5.0 to 8.5.

7. The method of claim 1, wherein the first precipitating agent is a fatty acid used with a salt.

8. The method of claim 7, wherein the fatty acid is caprylic acid.

9. The method of claim 8 wherein the fatty acid is present in step (a) in a concentration of from about 0.1% to about 10% (v/v).

10. The method of claim 9 wherein the fatty acid is present in step (a) in a concentration of about 1%.

11. The method of claim 1, wherein the pH in step (a) is from about 4 to about 6.

12. The method of claim 11, wherein the pH in step (a) is from about 4.5 to about 5.5.

13. The method of claim 7, wherein the salt is sodium acetate or sodium citrate.

14. The method of claim 1, wherein the first precipitating agent is calcium chloride.

15. The method of claim 1 further comprising subsequent to steps (a) and (b), subsequently precipitating impurities with calcium chloride as step (c).

16. The method of claim 15, wherein the concentration of calcium chloride is from about 10 mM to about 400 mM.

17. The method of claim 15, wherein the pH in step (c) is from about 6 to about 9.

18. The method of claim 1, further comprising a subsequent precipitation using cold ethanol.

19. The method of claim 15, further comprising a subsequent precipitation using cold ethanol.

20. The method of claim 1, wherein the protein of interest is an antibody.

21. The method of claim 1, wherein the antibody is immunoglobulin G.

22. The method of claim 1, wherein said method is carried out using a two-step precipitation reactor, optionally wherein the two steps are continuous.

23. The method of claim 1, performed without using chromatography.

24. The method of claim 15, performed without using chromatography.

25. The method of claim 19, performed without using chromatography.

26. The method of claim 14, wherein the PEG is introduced into the secondary cell culture supernatant in an amount of from about 10 to about 21%.

* * * * *